US011209357B2

United States Patent
Kojima et al.

(10) Patent No.: US 11,209,357 B2
(45) Date of Patent: Dec. 28, 2021

(54) METHOD FOR DIAGNOSING DETERIORATION OF LUBRICANT, AND SYSTEM AND METHOD FOR MONITORING LUBRICANT OF ROTATING MACHINE

(71) Applicant: HITACHI, LTD., Tokyo (JP)

(72) Inventors: Kyoko Kojima, Tokyo (JP); Mitsuru Saeki, Tokyo (JP); Shinichiro Aikawa, Tokyo (JP); Yasuki Kita, Tokyo (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 16/649,257

(22) PCT Filed: Aug. 22, 2018

(86) PCT No.: PCT/JP2018/030952
§ 371 (c)(1),
(2) Date: Mar. 20, 2020

(87) PCT Pub. No.: WO2019/082486
PCT Pub. Date: May 2, 2019

(65) Prior Publication Data
US 2020/0292450 A1 Sep. 17, 2020

(30) Foreign Application Priority Data
Oct. 27, 2017 (JP) .............................. JP2017-208062

(51) Int. Cl.
*G01N 21/51* (2006.01)
(52) U.S. Cl.
CPC .................................. *G01N 21/51* (2013.01)
(58) Field of Classification Search
CPC ...... G01N 21/27; G01N 21/51; G01N 21/251; G01N 21/78; G01N 21/94; G01N 33/2888

(Continued)

(56) References Cited

U.S. PATENT DOCUMENTS

| 5,139,330 A | 8/1992 | Niizawa et al. |
| 5,919,707 A | 7/1999 | Banks et al. |

(Continued)

FOREIGN PATENT DOCUMENTS

| CN | 104764489 A | 7/2015 |
| JP | 63-63967 A | 3/1988 |

(Continued)

OTHER PUBLICATIONS

Taiwan Office Action (Application No. 107136147) dated Mar. 7, 2019.

(Continued)

*Primary Examiner* — Tri T Ton
(74) *Attorney, Agent, or Firm* — Volpe Koenig

(57) ABSTRACT

A method for diagnosing the deterioration of a lubricant, and a system and method for monitoring a lubricant of a rotating machine are capable of diagnosing the deterioration of an additive to a lubricant. The concentration of the additive to the lubricant is obtained by using chromaticity data obtained on the basis of measurement data from an optical sensor, and, on the basis thereof, the deterioration of the lubricant is diagnosed. In addition, the system for monitoring the lubricant is provided with an optical sensor, an input device, a processing device, a storage device, and an output device. The storage device stores, in a time series, the concentration of the additive to the lubricant, which is obtained with the optical sensor, and the processing device estimates the time at which the concentration of the additive reaches a threshold value on the basis of concentration data of the additive.

15 Claims, 14 Drawing Sheets

(58) Field of Classification Search
USPC .................. 356/338, 410–415, 432–442
See application file for complete search history.

(56) References Cited

U.S. PATENT DOCUMENTS

| | | | |
|---|---|---|---|
| 9,063,075 | B2 | 6/2015 | Gorritxategi et al. |
| 2003/0060984 | A1* | 3/2003 | Takezawa .......... G01N 21/3577 |
| | | | 702/28 |
| 2012/0086942 | A1 | 4/2012 | Honda et al. |
| 2013/0068965 | A1* | 3/2013 | Yoshida ................ G01N 21/64 |
| | | | 250/458.1 |
| 2013/0250281 | A1 | 9/2013 | Shirata |
| 2013/0250303 | A1* | 9/2013 | Shirata ................ F16H 57/0405 |
| | | | 356/436 |
| 2014/0007657 | A1 | 1/2014 | Matsubara et al. |
| 2015/0115983 | A1 | 4/2015 | Potyrailo et al. |
| 2016/0041088 | A1 | 2/2016 | Ohnuma et al. |
| 2016/0054288 | A1 | 2/2016 | ODonnell |
| 2017/0307584 | A1 | 10/2017 | Hegazi et al. |
| 2018/0003618 | A1 | 1/2018 | Shinoda |

FOREIGN PATENT DOCUMENTS

| | | | |
|---|---|---|---|
| JP | H05-10871 | A | 1/1993 |
| JP | H05-223729 | A | 8/1993 |
| JP | 06-034541 | A2 | 2/1994 |
| JP | H07-294425 | A | 11/1995 |
| JP | 2000-292345 | A | 10/2000 |
| JP | 2007-046932 | A | 2/2007 |
| JP | 2008-026046 | A | 2/2008 |
| JP | 2008-045918 | A | 2/2008 |
| JP | 2012-117951 | A | 6/2012 |
| JP | 2012-181168 | A | 9/2012 |
| JP | 2013-156170 | A | 8/2013 |
| JP | 2013-536939 | A | 9/2013 |
| JP | 2015-064215 | A | 4/2015 |
| JP | 2016-014091 | A | 1/2016 |
| JP | 2016-044681 | A | 4/2016 |
| JP | 2016-126007 | A | 7/2016 |
| JP | 2017-111860 | A | 6/2017 |
| NO | 2013/099779 | A1 | 7/2013 |
| NO | 2016/114302 | A1 | 7/2016 |
| WO | 2010/150526 | A1 | 12/2010 |
| WO | 2013/191273 | A1 | 12/2013 |

OTHER PUBLICATIONS

Taiwan Office Action (Application No. 107136147) dated Aug. 1, 2019.
International Search Report for PCT/JP2018/030952, dated Nov. 20, 2018.
Japanese Office Action dated Sep. 23, 2020 for Japanese Patent Application No. 2017-208062.
Extended European Search Report dated Jul. 5, 2021 for European Patent Application No. 18869488.9.
Japanese Office Action dated May 11, 2021 for Japanese Patent Application No. 2017-208062.

* cited by examiner

METHOD FOR DIAGNOSING DETERIORATION OF LUBRICANT, AND SYSTEM AND METHOD FOR MONITORING LUBRICANT OF ROTATING MACHINE

TECHNICAL FIELD

The present invention relates to a method for diagnosing deterioration of a lubricant and a system and method for monitoring a lubricant of a rotating machine, and more particularly relates to a technique for diagnosing deterioration of a lubricant used in a rotating machine such as a wind power generator.

BACKGROUND ART

Diagnosis of deterioration of a lubricant is an important technique in performing maintenance of a rotating machine.

Examples of deterioration of a lubricant include deterioration due to oxidation of base oil, deterioration due to a contaminant, deterioration due to water entry, deterioration of an additive. Conventionally, as diagnosis of deterioration of a lubricant, there have been those described, for example, in Patent Documents (PTLs) 1 to 5.

PTL 1 discloses a system that measures a resonance impedance spectral response of an LCR resonator for a fluid and detects the presence of water, soot, wear products, and the like.

PTL 2 discloses a method of monitoring the state of deterioration of an oil in such a way that a lubricant or the like used in various machines or facilities is filtrated by a filter, an oil content is removed from the filter that has captured a contamination matter, light is emitted to the filter from which the oil content has been removed, and color components of transmitted light that has passed through the filter from which the coil content has been removed are detected.

PTL 3 discloses that the type of a contaminant in a lubricant is specified on the basis of a color detected by an optical sensor.

PTL 4 discloses monitoring the concentration of water mixed in a lubricant with an electrostatic capacitance detection means.

PTL 5 discloses monitoring a lubricating oil from a wind turbine by determining an initial ideal remaining life for the lubricating oil from the wind turbine; determining a temperature-based remaining life for the lubricating oil on the basis of a temperature measurement value of the lubricating oil from the wind turbine; calculating a contamination factor of the lubricating oil on the basis of a contamination sample of the lubricating oil; determining an updated ideal remaining life for the lubricating oil on the basis of the contamination factor, the initial ideal remaining life, and the temperature-based remaining life; and determining an actual remaining life for the lubricating oil on the basis of the updated ideal remaining life and a life loss factor. The contamination factor based on the contamination sample is calculated on the basis of properties of the lubricating oil (at least one measurement value of a ferrous particle count, water content, dielectric constant, and an international organization for standardization (ISO) particle level).

In addition, PTL 6 describes a method of managing a lubricant in such a way that both of two determination methods: a method of determining a deterioration degree of a lubricant from the content of an antioxidant in the lubricant determined using a Fourier transform infrared spectrometer (determination method a) and a method of measuring a color difference of substances captured when the lubricant is filtrated by a filter or a color difference of the lubricant using a colorimeter to determine a deterioration degree and a mixture degree of foreign substances on the basis of the color difference (determination method b), are used to determine a degradation degree of a lubricant containing an antioxidant.

CITATION LIST

Patent Literature

PTL 1: JP 2016-126007 A
PTL 2: WO 2010/150526
PTL 3: JP 2012-117951 A
PTL 4: JP 2012-181168 A
PTL 5: JP 2016-044681 A
PTL 6: WO 2016/114302

SUMMARY OF INVENTION

Technical Problem

Lubricants contain various additives to maintain the lubrication performance. For example, when lubrication conditions are severe and the pressure at a contact portion is high, when the sliding speed is low, or when the viscosity of the oil is too low, the film of the lubricant between friction surfaces becomes thin and the friction resistance increases, resulting in wear. This state is called boundary lubrication, and seizure occurs in extreme cases. An oil agent, an antiwear agent, and an extreme pressure additive (extreme pressure agent) act to reduce friction and wear in such boundary lubrication state, and these may collectively be called a load bearing additive. In addition, as another additive, there are, for example, an antioxidant and a defoamer.

For maintenance of desired lubrication performance, it is required that an additive be contained at a predetermined ratio (concentration) relative to a lubricant. Conventionally, as diagnosis of deterioration of a lubricant, there have been many proposals that detect deterioration due to a contaminant, deterioration due to water entry, and the like as described in PTLs 1 to 5. However, there has not been a proposal that is effective with regard to a method for diagnosing deterioration of additives (reduction of additives) of a lubricant.

In addition, PTL 6 proposes a method for determining deterioration of a lubricant containing an antioxidant. However, because it is determination using a Fourier transform infrared spectrometer, it is difficult to say that it is a simple diagnosis. In addition, diagnosis of deterioration of a lubricant including an extreme pressure agent as an additive is not taken into consideration. Furthermore, it cannot be used for online remote diagnosis of a lubricant used for a wind power generator or the like installed in a mountainous region or on the sea.

It is an object of the present invention to provide a method for diagnosing deterioration of a lubricant, and a system and method for monitoring a lubricant of a rotating machine that can diagnose deterioration of additives of a lubricant.

Solution to Problem

The present invention diagnoses deterioration of additives of a lubricant using chromaticity data determined on the basis of measurement data of an optical sensor.

Advantageous Effects of Invention

According to the present invention, it is possible to diagnose deterioration of additives of a lubricant. Problems, configurations, and effects other than those described above will be clarified by description of an embodiment below.

DESCRIPTION OF EMBODIMENTS

First, before an embodiment of the present invention is described in detail, the background that led to the present invention is described.

In recent years, preventive maintenance and planned maintenance of machines with rotating components (hereinafter referred to as rotating machines) have become widespread due to advances in technologies for evaluating the remaining life of components, A reduction in lubrication function due to oxidative deterioration of a lubricant and contamination particles such as abrasion powder and dust in a lubricant induce wear damage to rotating components such as bearings and gears, which leads to failure of the rotating machine. Therefore, a lubricant monitoring technique is particularly important.

A wind power generator, which is an example of an apparatus to which the present invention is applied, uses a lubricant or the like to reduce a coefficient of mechanical friction between constituent elements. A lubricant monitoring technique will be described below by taking an example of a lubricant of a wind power generator.

Figure 1:
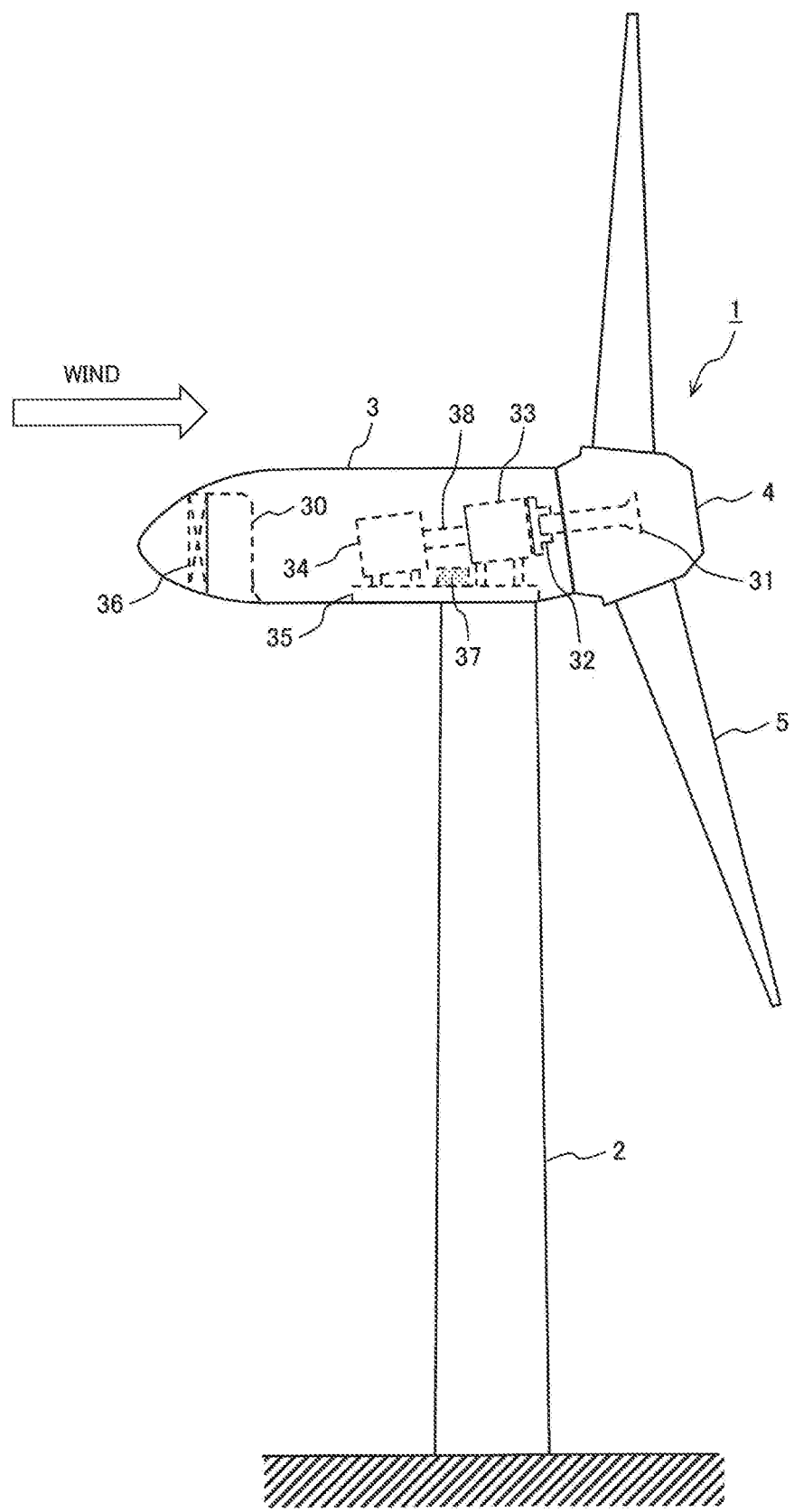
FIG. 1 is a schematic overall configuration view of a wind power generator, which is an example of an apparatus to which the present invention is applied.

FIG. 1 illustrates a schematic overall configuration view of a downwind type wind power generator. In FIG. 1, each equipment disposed in a nacelle 3 is indicated by the dotted lines. As illustrated in FIG. 1, a wind power generator 1 includes blades 5 that receive wind and rotate, a hub 4 that supports the blades 5, the nacelle 3, and a tower 2 that rotatably supports the nacelle 3 in a horizontal plane.

The nacelle 3 includes therein a main shaft 31 that is connected to the hub 4 and rotates together with the hub 4, a shrink disc 32 coupled to the main shaft 31, a speed increaser 33 that is connected to the main shaft 31 via the shrink disc 32 and increases the rotation speed, and a generator 34 that rotates a rotor at a rotation speed increased by the speed increaser 33 via a coupling 38 and performs a power generation operation.

A portion that transmits the rotation energy of the blades 5 to the generator 34 is called a power transmission portion. In the present example, the main shaft 31, the shrink disc 32, the speed increaser 33, and the coupling 38 are included in the power transmission portion. The speed increaser 33 and the generator 34 are held on a main frame 35. In addition, one or more oil tanks 37 that store a lubricant for lubrication of the power transmission portion are set on the main frame 35. In addition, in the nacelle 3, a radiator 36 is arranged on the windward side of a nacelle partition 30. Cooling water cooled by the radiator 36 using outdoor air is circulated to the generator 34 and the speed increaser 33 to cool the generator 34 and the speed increaser 33.

In a wind power generator, a lubricant is used for many rotating components. For example, in FIG. 1, a lubricant is supplied to the main shaft 31, the speed increaser 33, the generator 34, and yaw, pitch etc. bearings, which are not illustrated. Controlling output by changing a pitch angle of the blades depending on a wind speed is pitch control of the blades, and orientation control of the nacelle is yaw control.

It is necessary to supply a lubricant to such movable portions. The lubricant reduces friction of the rotating portion and prevents wear, damage, or energy loss of the components. However, a reduction in lubrication performance due to aging deterioration of the lubricant or contamination due to mixture of abrasion particles, dust, or the like into the lubricant increases the coefficient of friction, resulting in an increase in risk of failure of the wind power generator.

When failure of the wind power generator occurs, a considerable loss cost is generated, e.g., the cost due to replacement of faulty components and a reduction in power generation income during power outage. Thus, measures including early component preparation and power outage period reduction by remaining life prediction and sign detection are desired. In particular, for the speed increaser, which is an important component, a reduction in performance of the lubricant increases a failure risk. Therefore, a technique for estimating the remaining life and a replacement period of the lubricant as early as possible is important.

Conceivable parameters to be monitored for evaluating the property of the lubricant would be various matters such as viscosity, total acid number measurement, component element analysis.

However, when it is assumed that the lubricant of the wind power generator is to be monitored, for example, by the evaluation of the property using viscosity, because the lubricant for the speed increaser of the wind turbine generator uses a chemically very stable synthetic oil, the viscosity barely changes, and this alone is not appropriate as an index of the remaining life estimation. In addition, for measurement of a total acid number indicating deterioration due to oxidation, because the lubricant for the speed increaser of the wind turbine generator uses a synthetic oil that is very stable with respect to oxidation, and the total acid number barely changes, and this alone is not appropriate as an index of the remaining life estimation.

In addition, another conceivable method would be to measure particle powder or water content contained in the lubricant. However, there is a possibility that wear or leak has already occurred at the point of time when such content is detected in the lubricant, and earlier detection of a sign is desired. In addition, the lubricant for the speed increaser of the wind turbine generator has high viscosity and is circulated in a state where a large number of bubbles is mixed. By a particle measurement method that measures particles by setting a particle counter or an iron powder concentration meter, it is difficult to distinguish between bubbles and particles. In addition, it is in principle impossible to measure consumption of the additives of the lubricant to be described below using a particle counter or an iron powder concentration meter.

In view of the above, for early estimation of the remaining life of the lubricant of the wind power generator, a new performance evaluation method for the lubricant of the wind power generator is needed.

Incidentally, as described above, the lubricant contains various additives for maintaining the lubrication performance, such as a load bearing additive, e.g., an oil agent, an antiwear agent, and an extreme pressure additive (extreme pressure agent), an antioxidant, or a defoamer. The lubricant for the speed increaser of the wind power generator contains one or more of these additives.

The oil agent is adsorbed to a metal surface and forms an adsorption film. This adsorption film prevents direct contact between metals, which are in a boundary lubrication state, and acts to reduce friction and wear. As the oil agent, a higher fatty acid, higher alcohol, amine, ester, metal soap, or the like, which have a high adsorption power with respect to a metal surface, are used.

The antiwear agent is effective for wear prevention under loading conditions that are more severe than those of the oil agent. In general, phosphate ester, phosphorous ester, and thiophosphate are often used. The antiwear agent is used for a turbine oil, a wear resistance hydraulic fluid, or the like. In particular, zinc dialkyldithiophosphate (ZnDTP, also called ZDDP) also has an antioxidant performance.

At the contact surface in a high loading state where the boundary lubrication state is under the severest condition, the friction surface has very high temperatures, and the adsorption film of the oil agent is desorbed to be ineffective. However, because the extreme pressure additive is a chemically active substance including sulfur, chlorine, and phosphorus, it reacts with a metal surface and produces a compound including sulfur, chlorine, and phosphorus, thereby becoming a coating having a small shear force to prevent wear, seizure, and fusion.

As the extreme pressure additive, generally, in addition to sulfurized oil, sulfurized ester, sulfide, and chlorinated hydrocarbon, a substance containing sulfur, chlorine, phosphorus, or the like, e.g., lead naphthenate, or a compound including two or more elements of sulfur, phosphorus, and chlorine in the same molecule is also used. Specific extreme pressure additives include sulfurized sperm oil, sulfurized fatty ester, dibenzyldisulfide, alkylpolysulfide, olefin polysulfide, xanthic sulfide, chlorinated paraffin, methyl trichlorostearate, lead naphthenate, amine alkylthiophosphate, chloroalkyl xanthate, phenol thiocarbamate, triphenylphosphorothionate (TPPT), 4,4'-methylene bis(dithiocarbamate).

The antioxidant is used to prevent deterioration due to oxidation of a base oil. There are three types of antioxidant: a free radical inhibitor that suppresses generation of a free radical at the initial stage of oxidation and stops the chain of oxidation reaction of hydrocarbons, a peroxide decomposer that plays a role to decompose a generated peroxide to change it into a stable non-radical compound, and a metal deactivator that produces a strong adsorption film (inert anticorrosion coating). The role of the metal deactivator is to prevent dissolution of iron or copper by metal corrosion property of the peroxide generated by oxidation of the lubricant.

Specific antioxidants include a phenol derivative (e.g., 2,6-di-tert-butyl p-cresol (BHT), 2,6-di-tert-butyl p-phenol (DBP), or 4,4'-methylene bis(2,6-dialkylphenol)), an amine derivative (e.g., 2,6-diallyl-α-dimethylamino paracresol, 4,4'-tetramethyldiaminodiphenylmetane, octylated phenylnaphthylamine, di-octyl-diphenylamine, dinonyl-diphenylamine, phenothiazine, 2,2,4-trimethyldihydroxyquinizarin), metal dithiophosphate, alkyl sulfide, or the like, 1,4-dioxydianthraquinone (also known quinizarin), 1,2-dioxydianthraquinone (also known as: alizarin), benzotriazole, and alkylbenzotriazole.

As examples of the defoamer, a silicone-based defoamer, surfactant, polyether, and higher alcohol are known. In a high-viscosity lubricant such as a gear oil, bubbles, when generated, are hard to disappear, providing influences such as generation of damage to components, generation of cavitation, a reduction in hydraulic efficiency, a reduction in cooling capacity due to a reduction in lubrication performance.

These additives need to be contained at a predetermined ratio (concentration) with respect to the lubricant for maintenance of a desired lubrication performance. However, as described above, conventionally, as described in PTLs 1 to 5, there have been many proposals that detect deterioration due to a contaminant, deterioration due to water entry, and the like. However, there was no direct measurement of a change in component of the lubricant itself, particularly the concentration of the additives of the lubricant.

Thus, the inventors made comparison and study with regard to a method of performing diagnosis of a sign of deterioration of the lubricant by monitoring the state, particularly the transition of the concentration of the additives contained in the lubricant.

Figure 2:
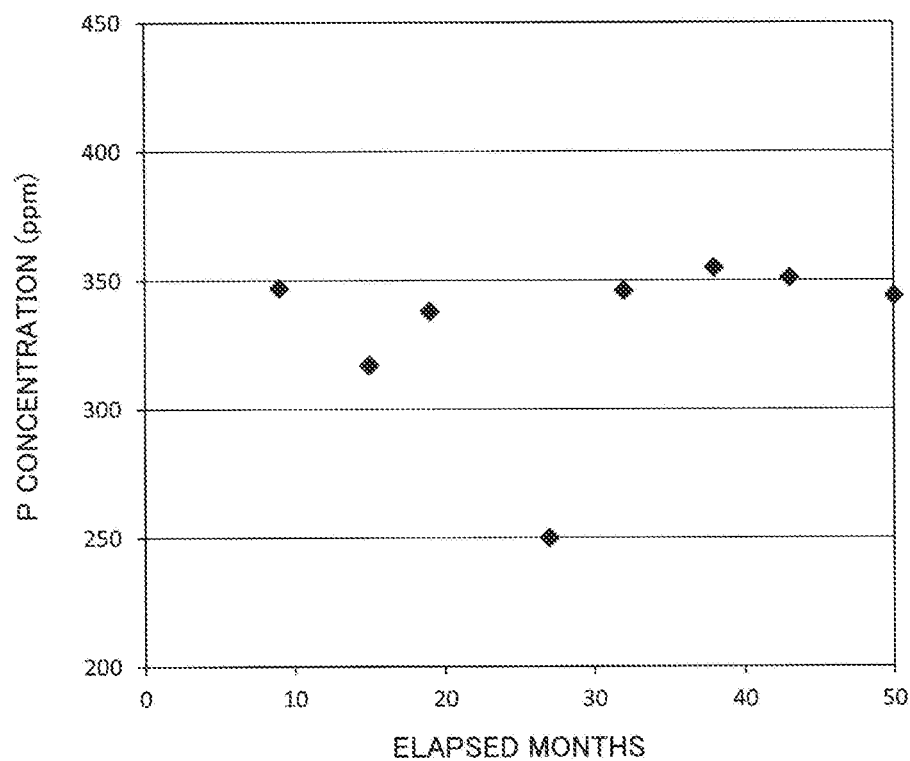
FIG. 2 is a graph illustrating a result of measurement of phosphorus concentration in a lubricant by ICP elemental analysis.

FIG. 2 illustrates a result of measurement of concentration of phosphorus, which is a component of the extreme pressure additive in the lubricant by ICP (inductively coupled plasma) element analysis, which is known as one of component analysis methods. The horizontal axis is elapsed time (months) and the vertical axis is phosphorus (P) concentration (ppm). This result does not show any significant relationship between the elapsed time and the phosphorus concentration. This suggests that the element analysis precision is insufficient as precision for sign diagnosis.

According to the result of measurement illustrated in FIG. 2, the phosphorus concentration once reduced is increased again. It is unlikely that the concentration of the extreme pressure additive increases spontaneously. A conceivable factor of such measurement result is that the ICP elemental analysis also measures a phosphoric acid, which is a decomposition product of the extreme pressure additive. In addition, because the ICP elemental analysis turns a specimen into plasma, a liquid component (the lubricant, the additives, decomposition products of the additives, or the like) and a solid component (the abrasion powder or the like) are analyzed together, it is not considered to be suitable for quantifying the components of the additives in the lubricant.

Figure 3:
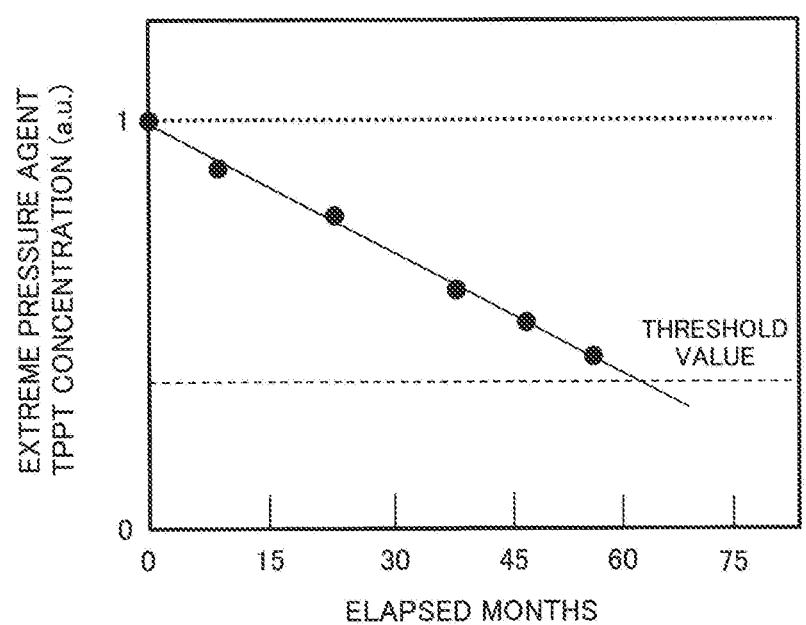
FIG. 3 is a graph illustrating a result of measurement of concentration of a phosphorus-based extreme pressure additive in a lubricant obtained by LC measurement.

FIG. 3 is a graph illustrating a result of consumption behavior (reduction) of a phosphorous-based extreme pressure additive in the lubricant in association with a wind turbine operation obtained by LC/MS (liquid chromatography-mass spectrometry). In this example, the phosphorous-based extreme pressure additive is specifically TPPT. The horizontal axis is elapsed time (months) and the vertical axis is TPPT concentration (relative value relative to new oil). This results shows a significant relationship between the elapsed time and the concentration—a linear reduction in concentration in association with the elapsed months.

In the LC measurement, a sample in a liquid state is subject to separation of components by the principle of chromatography. Next, the separated components are detected by a UV detector, a refractive index detector, and a mass spectrometer. The LC measurement is suitable for qualifying and quantifying an organic compound. In particular, when a mass spectrometer is used for the detector, only the additives in the lubricant can be quantified with high precision and high sensitivity.

According to the above study, it was found that, in order to monitor a change in concentration of the additives in the lubricant over time to be able to maintain and manage the functions of the additives, a measurement method that can directly measure the concentration of the additives in the lubricant such as the LC measurement is suitable. In addition, it was found that, when the concentration of the additives in the lubricant falls below a predetermined threshold value, the performance of the lubricant becomes insufficient, resulting in failure of the apparatus.

Given the above, as a new performance evaluation method for the lubricant of a wind power generator for early estimation of the remaining life of the lubricant of the wind power generator, measurement of the concentration of the additives in the lubricant is effective.

In addition to the LC measurement, a method that can directly accurately measure the concentration of the additives in the lubricant includes Fourier transform infrared spectroscopy (FT-IR), nuclear magnetic resonance (NMR), and the like.

When the concentration of the additives in the lubricant is directly measured accurately by LC/MS, FT-IR, NMR, or the like, the deterioration (reduction) of the additives of the lubricant can be monitored. However, these analysis methods require time for analysis. Therefore, it is desired that the concentration of the additives of the lubricant be accurately measured briefly. In addition, because wind power generators are often installed in a mountainous region or on the sea, it is desired that the concentration of the additives of the lubricant be measured by online remote monitoring.

As a result of various studies, the inventor found that the concentration of the additives of the lubricant can be measured using chromaticity data determined on the basis of measurement data of an optical sensor.

A sensor that monitors the deterioration of the lubricant includes an optical sensor described, for example, in PTL 3. The optical sensor includes a light source, e.g., a white LED, that emits visible light and a visible light reception element (RGB color sensor). The optical sensor measures the transmittance of the visible light that passes through the lubricant and measures the chromaticity of the lubricant.

Figure 4:
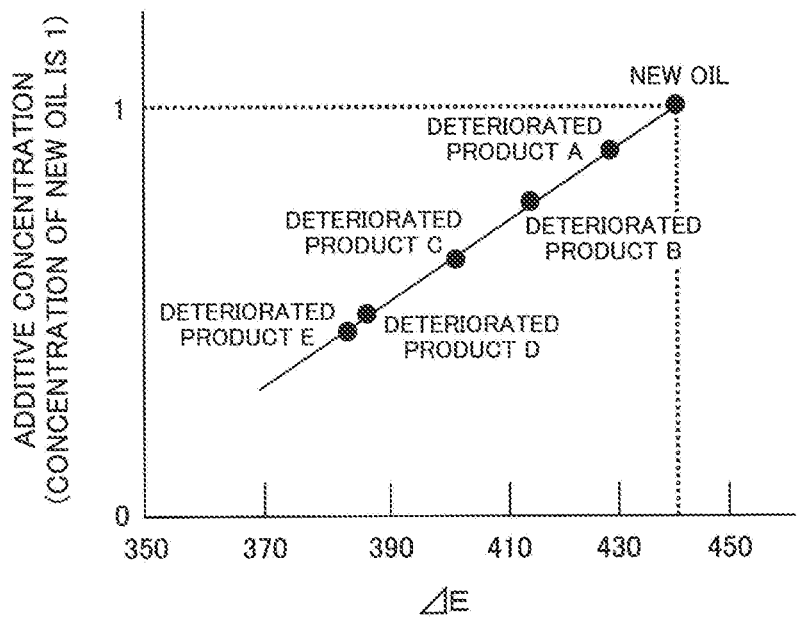
FIG. 4 is a graph illustrating a correlation between extreme pressure agent concentration in a lubricant and chromaticity.

As a result of a study by the inventor, it was found that the concentration of the additives in the lubricant determined by the LC measurement or the like and the degree of color (chromaticity) of the lubricant are correlated as illustrated in FIG. 4 (FIG. 4 illustrates a linear correlation, but it is not limited to linear correlation) FIG. 4 is a graph illustrating a correlation between the concentration of the extreme pressure agent in the lubricant and the chromaticity. The vertical axis indicates the concentration of the additives in the lubricant determined by the LC measurement or the like, and the horizontal axis indicates chromaticity determined on the basis of measurement data of the optical sensor. Here, the chromaticity in FIG. 4 is indicated by color difference ($\Delta E$) that is calculated by a color space formed by a combination of RGB. The definition of $\Delta E$ in FIG. 4 is $\Delta E=(R^2+G^2+B^2)^{1/2}$, and R, G, and B indicate three primary colors of light (red, green, blue) in the case of additive mixture and are expressed as (R,G,B) for indication of numerical values of a color coordinate. Note that RGB chromaticity encoded using 24 bpp (24 bit per pixel) is indicated by three 8-bit unsigned integers (0 to 255) indicating intensity of red, green, and blue. For example, (0, 0, 0) indicates black, (255, 255, 255) indicates white, (255, 0, 0) indicates red, (0, 255, 0) indicates green, and (0, 0, 255) indicates blue. Note that, in addition to an RGB colorimetric system, indication of chromaticity includes various types including an XYZ colorimetric system, an L*a*b* colorimetric system, and an L*u*v* colorimetric system. These can be mathematically converted and developed into various colorimetric systems, and therefore chromaticity may be indicated by another colorimetric system.

When a relationship between the concentration of the additives in the lubricant determined by the LC measurement or the like and the chromaticity of the lubricant determined on the basis of measurement data of the optical sensor is preliminarily determined as illustrated in FIG. 4 for each additive, for monitoring of the lubricant, the concentration of the additives of the lubricant can be measured on the basis of the chromaticity of the lubricant determined on the basis of the measurement data of the optical sensor. In this way, it is clarified that a reduction (degree of consumption) of the additives in the lubricant, which is an index of the deterioration of the lubricant, can be determined by the chromaticity measured by the optical sensor. Thus, as compared with analysis by LC/MS, FT-IR, NMR, or the like, the concentration of the additives of the lubricant can be measured briefly. In addition, installing the optical sensor in the nacelle also enables online remote monitoring of the lubricant of the wind power generator.

Figure 5:
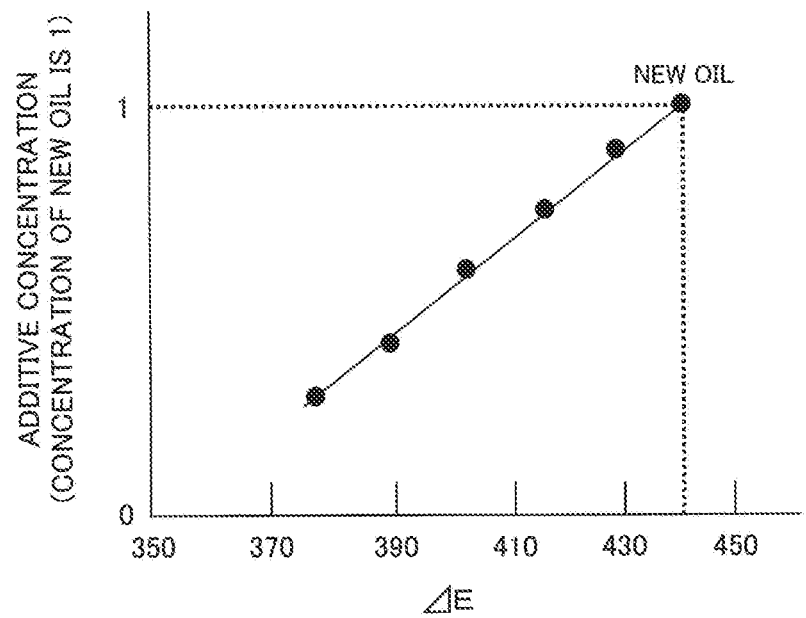
FIG. 5 is a graph illustrating a correlation between antioxidant concentration in a lubricant and chromaticity.

FIG. 4 illustrates the case were the lubricant contains the extreme pressure agent as the additive. As illustrated in FIG. 5 similarly, in the case where the lubricant contains an antioxidant as an additive, the additive concentration correlates with chromaticity. FIG. 5 is a graph illustrating a correlation between the concentration of an antioxidant in the lubricant and the chromaticity.

The reason why the degree of consumption of the additive, which is an index of the deterioration of the lubricant, correlates with the chromaticity is described below. The additive, when acting on a slide surface of a gear or a bearing, is decomposed, and the decomposition product of the additive is an oxidation product such as a phenolic oxide or quinone, which is colored in yellow to reddish brown. For example, when BHT, which is an antioxidant, or TPPT, which is an extreme pressure agent, is decomposed, a coloring compound is generated. BHT and TPPT are almost colorless. Given the above, the deterioration of the lubricant positively correlates with an increase in coloring compound, which is a decomposition product. Accordingly, chromaticity measurement determines the degree of deterioration of the lubricant.

Figure 6:
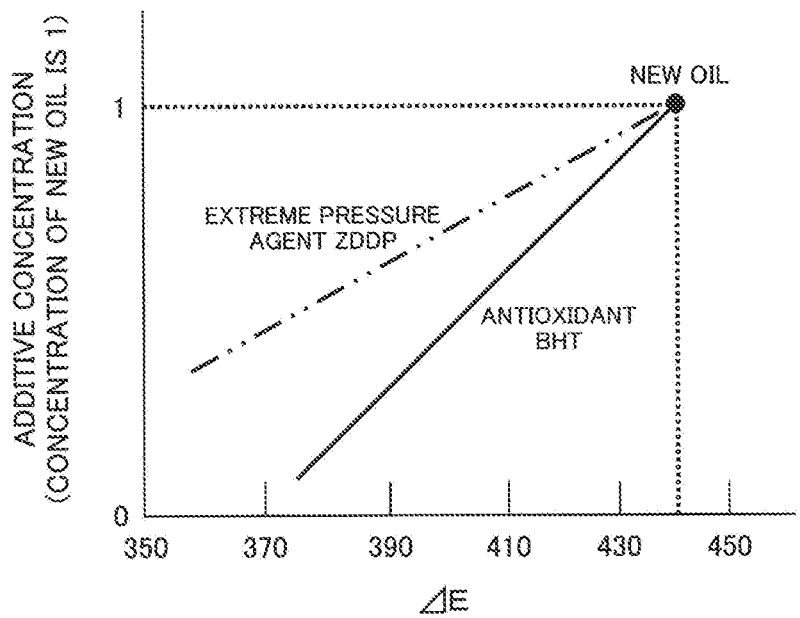
FIG. 6 is a graph illustrating a correlation between concentrations of two types of additives in a lubricant and chromaticity.

The lubricant can contain a plurality of additives. Similarly, in this case, when the relationship between the concentration of the additives in the lubricant determined by the LC measurement or the like and the chromaticity of the lubricant determined on the basis of measurement data of the optical sensor is preliminarily determined, for monitoring of the lubricant, the concentration of each additive in the lubricant can be measured on the basis of the chromaticity of the lubricant determined on the basis of the measurement data of the optical sensor. FIG. 6 is a graph illustrating a correlation between the concentration of each additive and the chromaticity in the case where two types of additives: an extreme pressure agent (ZDDP) and an antioxidant (BHT) are contained in the lubricant. As can be seen from this drawing, the consumption speed of the extreme pressure agent differs from that of the antioxidant. The concentration of such additives whose consumption speeds are different can also be measured on the basis of the chromaticity determined on the basis of measurement data of the measurement sensor.

Furthermore, the present inventor found that, on the basis of the measurement data of the optical sensor, the consumption (deterioration) of the additives of the lubricant and the contamination of the lubricant can be distinguished.

Figure 7:
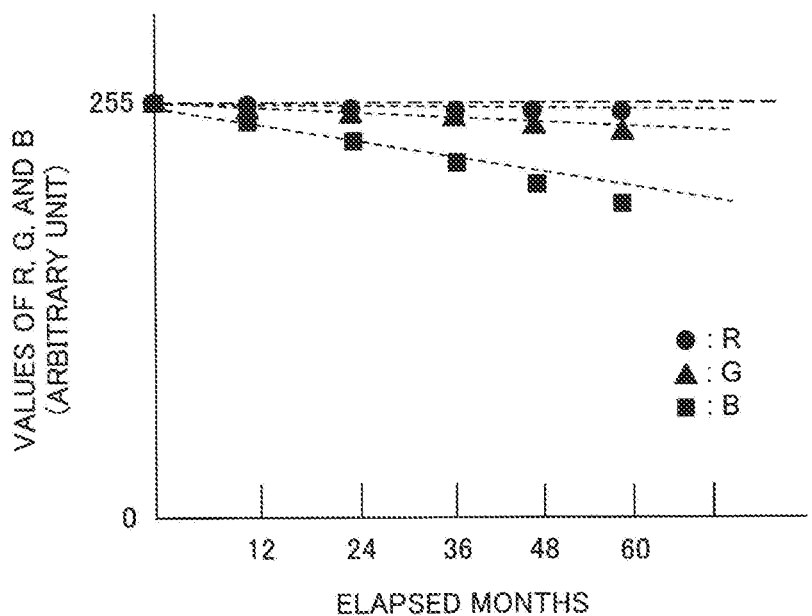
FIG. 7 is a graph illustrating a state of a change in each value of R, G, and B at the time when an additive in a lubricant is consumed (an additive is decomposed to produce an oxidation product).

FIG. 7 is a graph illustrating a state of a change in each value of R, G, and B at the time when the additives in the lubricant are consumed, i.e., the additives are decomposed to produce an oxidation product. The horizontal axis is elapsed time (months) and the vertical axis is values of R, G, and B. As illustrated in FIG. 7, regarding consumption of the additives, among R, G, and B, mainly a B value is largely reduced.

Figure 8:
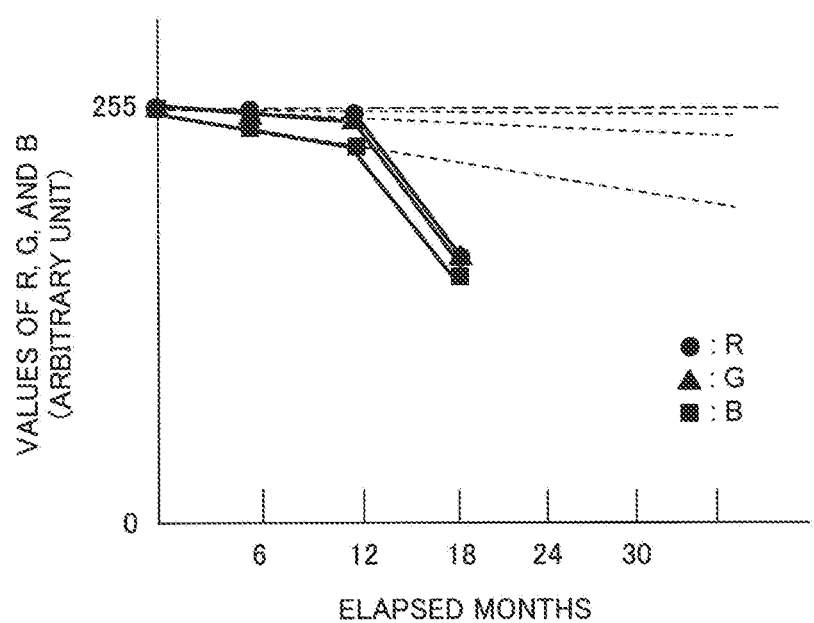
FIG. 8 is a graph illustrating a state of a change in each value of R, G, and B at the time when abrasion powder is generated in a lubricant.

Meanwhile, FIG. 8 is a graph illustrating a state of a change in each value of R, G, and B at the time when abrasion Powder is generated in the lubricant. Similar to FIG. 7, the horizontal axis is elapsed time (months) and the vertical axis is values of R, G, and B. As illustrated in FIG. 8, in the case of contamination, all values of R, G, and B are largely reduced. When lubricant contamination due to abrasion powder or dust occurs, such solids float in the lubricant, resulting in a reduction in visible light transmittance. Similarly, water entry causes the lubricant to be murky, the visible light transmittance is reduced. Accordingly, when the lubricant is measured by the optical sensor, in addition to measurement of the concentration of the additives of the lubricant, it is possible to detect lubricant contamination due to abrasion powder or dust, and contamination such as water entry. According to a change in each value of RGB, the deterioration and the contamination of the lubricant can be distinguished.

An embodiment of the present invention will be described in detail below in conjunction with the drawings. However, the present invention is not construed to be limited to the content described in the embodiment indicated below. A person skilled in the art would easily understand that the specific configuration can be changed without departing from the idea or gist of the present invention.

In a configuration of the invention described below, the same portions or portions having similar functions are denoted by the same reference numerals in different drawings, and redundant description may be omitted.

When there is a plurality of elements having the same or similar functions, the same reference numerals may be given different suffixes for description. However, if there is no need to distinguish between multiple elements, the description may be Given without suffixes.

Notations such as "first", "second", and "third" in the present specification and the like are used to distinguish constituent elements, and do not necessarily limit the number, order, or content thereof. In addition, the number for distinguishing a constituent element is used for each context, and the number used in one context does not necessarily indicate the same configuration in another context. In addition, a constituent element distinguished by one number will not be prevented from having the function of a constituent element distinguished by another number.

The position, size, shape, range, or the like of each configuration illustrated in the drawings or the like, in some cases, does not accurately represent the actual position, size, shape, range or the like for the sake of easy understanding of the invention. For this reason, the present invention is not necessarily limited to the position, size, shape, range, or the like disclosed in the drawings or the like.

EXAMPLE 1

The present example is applied to a system and method for monitoring a lubricant of wind power generator.

The present example is a system for monitoring a lubricant supplied to a mechanical drive portion of the wind power generator. The system includes an input apparatus, a processing apparatus, a storage apparatus, and an output apparatus. The storage apparatus stores additive concentration data that chronologically stores the concentration of additives of the lubricant. The processing apparatus estimates time for the concentration of the additives in the lubricant determined by chromaticity characteristics of the lubricant to be a predetermined threshold value on the basis of data of the optical sensor that can quantify the concentration of the additives in the lubricant and measure the chromaticity of the lubricant.

In addition, the present example is a method for monitoring the lubricant of the wind power generator using an optical lubricant sensor using a server including the processing apparatus, the storage apparatus, the input apparatus, and the output apparatus. This method executes a first step that acquires chromaticity data of the lubricant of the wind power generator, a second step that measures the concentration of the additives contained in a sample, a third step that chronologically stores the measured concentration of the additives in the storage apparatus to obtain additive concentration data, and a fourth step in which the processing apparatus processes the additive concentration data to estimate time for the concentration of the additives to be a predetermined threshold value.

(1. Overall system configuration)

Figure 9:
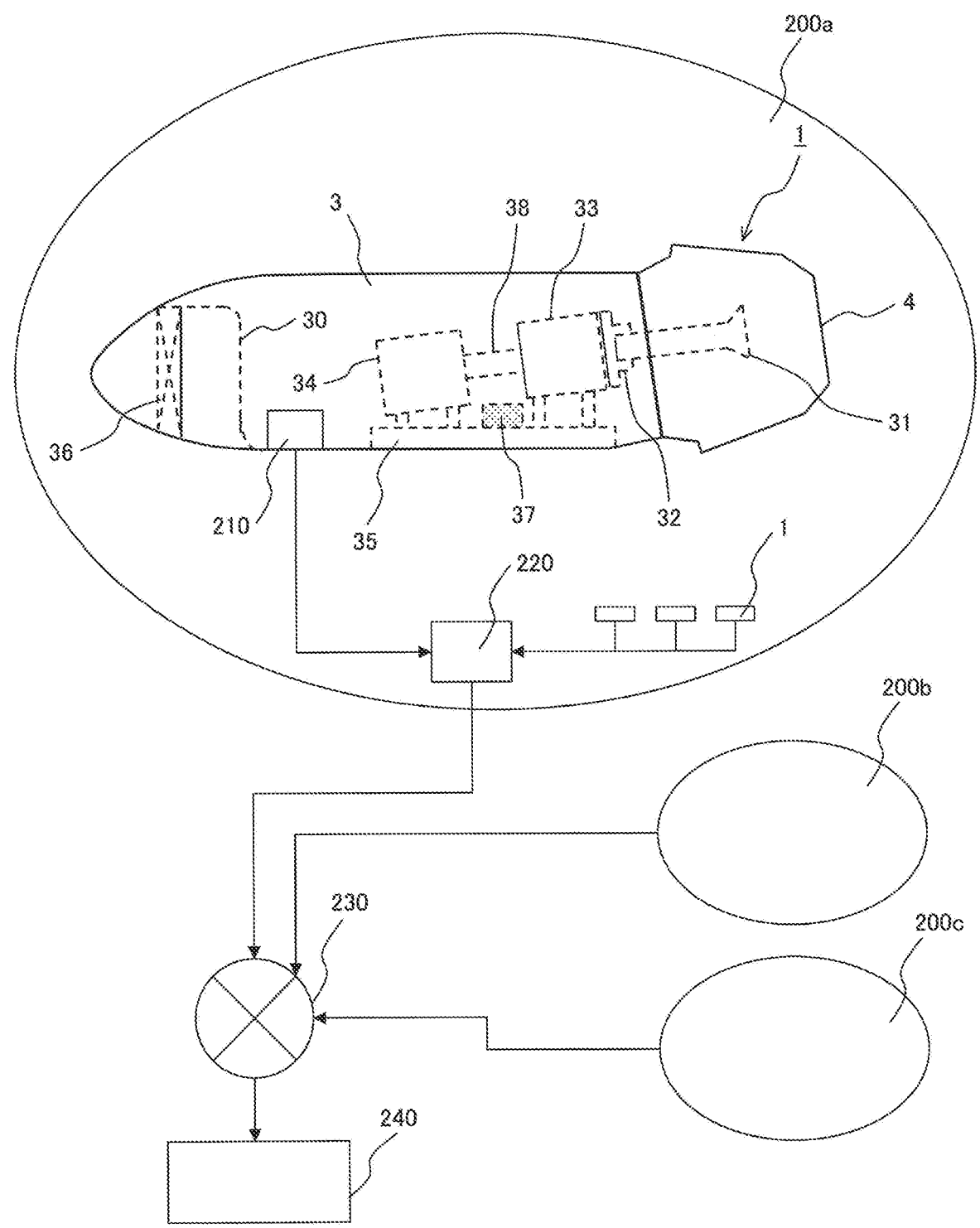
FIG. 9 is a schematic view of a monitoring system for a lubricant of a wind power generator including a lubricant supply system.

FIG. 9 illustrates a schematic view of a system for monitoring a lubricant of a wind power generator having a lubricant supply system. For the sake of description, FIG. 9 illustrates the nacelle 3 portion of the wind power generator 1 extracted from FIG. 1. The nacelle 3 includes therein the main shaft 31, the speed increaser 33, the generator 34, and yaw, pitch etc. bearings, which are not illustrated, to which a lubricant is supplied from the oil tank 37.

As illustrated in FIG. 9, typically, a plurality of wind power generators 1 is set on the same site, and they are collectively called a farm 200a or the like. Each wind power generator 1 includes various sensors (not illustrated) on the lubricant supply system. Sensor signals reflecting the state of the lubricant are aggregated to a server 210 in the nacelle 3. In addition, sensor signals obtained from the server 210 of each wind power generator 1 are sent to an aggregation server 220 that is arranged for each farm. The data from the aggregation server 220 is sent to a central server 240 via a network 230. Data from another farm 200b or 200c is also sent to the central server 240. In addition, the central server 240 can send an instruction to each wind power generator 1 via the aggregation server 220 or the server 210.

(2. Sensor Arrangement)

Figure 10:
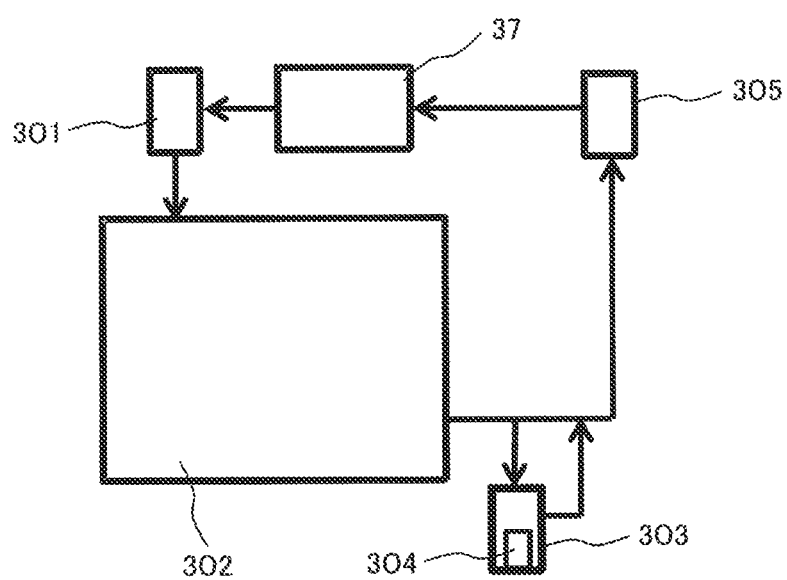
FIG. 10 is a conceptual view of a rotating component including a lubricant sensor.

FIG. 10 is a conceptual diagram of a rotating component including a lubricant sensor. The lubricant is supplied from a lubricant supply device 301, e.g., a pump, to a rotating component 302. The lubricant supply device 301 is connected to the oil tank 37 and receives supply of the lubricant. The rotating component 302 is, for example, the speed increaser 33 and a general portion where mechanical contact occurs, and is not particularly limited.

A sensor group 304 is arranged in a flow channel of the lubricant or the like for detecting the state of the lubricant. In the present example, a measurement portion 303 is provided in a flow channel (near the end of a lubricant path) branching off a lubricant flow channel connected to an oil discharge port for the lubricant of the rotating component 302, and part of the lubricant is introduced into the measurement portion 303. The sensor group 304 is installed in the measurement portion 303. The measurement portion 303 is not provided in a main lubricant flow channel such that the flow rate of the lubricant in the measurement portion 303 is adjusted to a flow rate suitable for detecting the state of the lubricant. The lubricant discharged from the rotating component 302 returns to the oil tank 37 via a filter 305. Note that the filter 305 is not essential. The sensor group 304 measures various parameters of the lubricant. For example, the physical amount includes temperature, hydraulic pressure, and the like. These can be measured using a publicly known sensor such as those disclosed, for example, in PTLs 1 to 5. The state of the lubricant can be evaluated on the basis of a temporal change in these parameters. A sensor for such temperature or the like is not essential in carrying out the present invention, but is preferably provided for detecting the state of the lubricant in more detail. In addition, for example, the sensor group 304 can include a sensor that measures information regarding contamination particles contained in the lubricant, e.g., a particle concentration. There is a high possibility that the particles are originated from wear of components, and the deterioration of the lubricant or abnormality of the apparatus can be detected. There is a possibility that an abnormality detected by the sensor that measures contamination particles is an abnormality that has already occurred, but the information of the sensor can be acquired in real-time, and monitoring is useful.

In the present example, the sensor group 304 includes an optical sensor including a visible light source and a reception element. By the optical sensor, chromaticity information (values of R, G, and B) of the lubricant is acquired.

According to the acquired chromaticity data, the amount of additives remaining in the lubricant is determined, and diagnosis of a degree of deterioration and diagnosis of remaining life are performed. In diagnosis using sensor data, diagnosis is performed on the basis of sensor data by the optical sensor or sensor data of the optical sensor and different one or more types of sensor data.

The lubricant when used has deteriorated quality and does not provide an initial function. Therefore, depending on a quality deterioration situation, maintenance such as replacement needs to be performed. It is useful in terms of efficiency of maintenance management to enable monitoring, at a remote site, of data that can be collected by the sensor group 304 installed at the actual site in order to know the timing of such maintenance. The data collected by the sensor group 304 is aggregated to, for example, the server 210 in the nacelle 3, then passes through the aggregation server 220 that aggregates data in the farm 200, and is sent to the central server 240 that aggregates data of a plurality of farms.

However, regarding analyses that require facilities for measurement, e.g., LC measurement, FT-IR measurement, and NMR measurement, a sample of the lubricant needs to be collected and analyzed Using a separately provided facility as appropriate. It is desirable that results of measurement by the LC measurement, FT-IR measurement, and NMR measurement be also separately stored in the central server 240 as data and the data be aggregated, and the property of the lubricant be understood in consideration of such data.

In addition, the data to be aggregated include not only data regarding the lubricant, but also data indicating an operation situation of the wind power generator. For example, it is a wind turbine output value (the larger, the higher the speed of deterioration of a lubricant), an actual operation time (the longer, the higher the speed of deterioration of a lubricant), a machine temperature (the higher, the higher the speed of deterioration of a lubricant), a rotation rate of the shaft (the higher, the higher the speed of deterioration of a lubricant), or the like. They can be collected from a sensor having a publicly known configuration installed at locations of the wind power generator or a control signal of the apparatus.

(3. Lubricant Diagnosis Flow)

Figure 11:
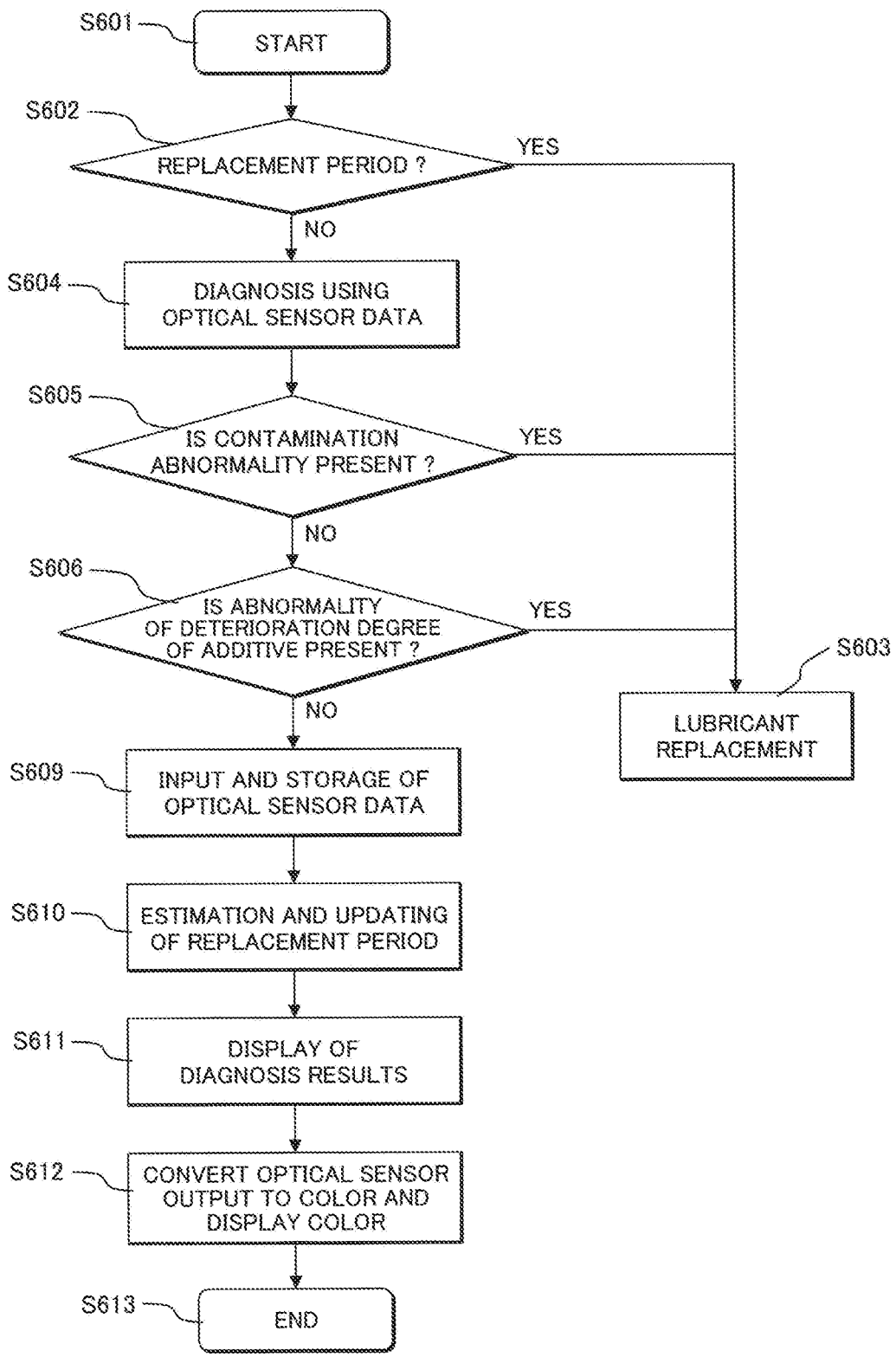
FIG. 11 is a lubricant diagnosis flowchart.

FIG. 11 is a flowchart illustrating lubricant diagnosis processing of the present example. The processing illustrated in FIG. 11 is performed under control by any of the server 210, the aggregation server 220, and the central server 240 of FIG. 9. In the example below, it is performed by the central server 240. Functions such as calculation and control are achieved when predetermined processing collaborates with another hardware when software stored in the storage apparatus of the server is executed by a processor. Note that functions equivalent to the functions configured by software can also be achieved by hardware such as FPGA (field programmable gate array), ASIC (application specific integrated circuit), or the like.

When the central server 240 performs control, because it has a plurality of wind power generators 1 under its control, the processing below is performed for each wind power generator. This processing is basically repetitive processing, and the start timing is set by a timer or the like. For example, the processing starts at 0 o'clock every day (S601). In addition, the central server 240 can perform it at any timing according to an operator's instruction.

In processing S602, the central server 240 checks a lubricant replacement period. The initial value of the replacement period is, for example, on the basis of the assumption that the lubricant is operated at design temperatures, physically calculated using the Arrhenius reaction rate, and the remaining life can be set initially. Regarding such calculation method, for example, there is description in PTL 5. This replacement period can be updated in processing S610 at a later stage on the basis of actual Measurement data.

When it is a lubricant replacement period, in processing S603, the lubricant is replaced. Lubricant replacement is usually an operation by a worker. Therefore, the central server 240 performs indication and notification to give an instruction to the worker for a period and a subject for replacement.

When it is not a lubricant replacement period, in processing S604, the central server 240 performs diagnosis using sensor data. As the sensor data, in addition to chromaticity information of the lubricant obtained by the optical sensor, temperature, hydraulic pressure, the concentration of particles contained in the lubricant, and the like can be used. The data collected by the sensor group 304 is sent to the central server 240, and, for example, the central server compares parameters obtained from the sensors with a preset threshold value to evaluate the property of the lubricant.

When results of the diagnosis in processing S605 and S606 are abnormal, the lubricant is replaced in processing S603. When there is no abnormality, the processing S609 is performed. In processing S605, when, for example, all the values of R, G, and B of the optical sensor are lower than the predetermined threshold value, it is determined that there is a contamination abnormality. However, a contamination abnormality may be determined using a conventional method that uses a sensor. In S606, the correlations between the additive concentration and the chromaticity illustrated in FIGS. 4 to 6 are used to determine that there is an abnormality in degree of deterioration of additives when the additive concentration determined by the chromaticity measured by the optical sensor is lower than the predetermined threshold value. Note that it is also possible to determine that there is an abnormality in degree of deterioration of additives when the chromaticity is smaller than the predetermined threshold value without determining the additive concentration by chromaticity.

In processing S609, chromaticity measurement data or the like is input to the central server 240, and the data is chronologically stored.

From a viewpoint of preventive maintenance and planned maintenance of the wind power generator, it is desirable that, before it is determined that there is an abnormality, sign diagnosis be performed regarding deterioration of the lubricant on the basis of a transition of the concentration of the additives contained in the lubricant.

Figure 12:
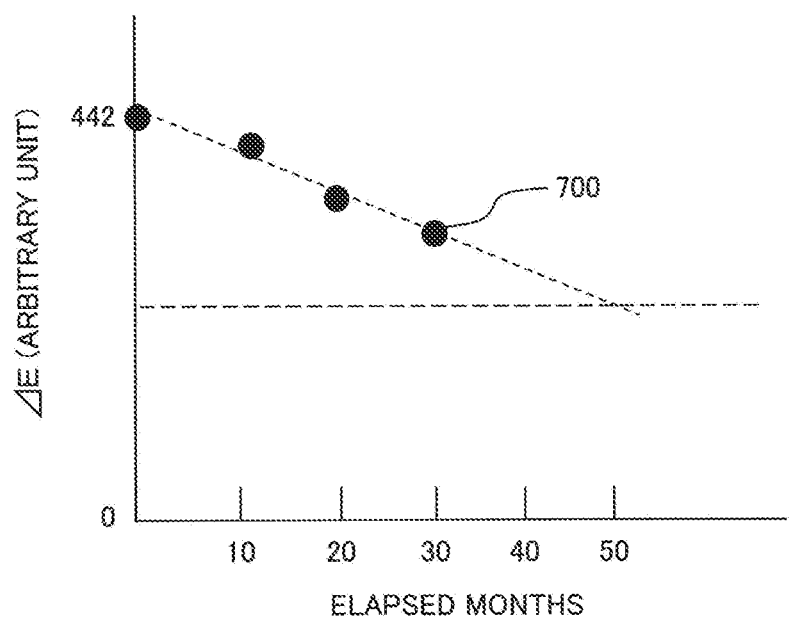
FIG. 12 is a graph illustrating a concept of lubricant remaining life estimation.

FIG. 12 is a graph illustrating a concept of a result of acquisition of chronologically stored lubricant chromaticity data. The horizontal axis indicates time (months) and the vertical axis indicates chromaticity (ΔE). For example, it is assumed that the chromaticity is subject to fixed-point observation, and chromaticity data 700 up to the elapse of 30 months is plotted. Similar to FIG. 3, a significant relationship is recognized between the elapsed time and the chromaticity, and, for example, the chromaticity is linearly reduced with time. According to the chromaticity data (values of (R,G,B)), by using the correlation between the chromaticity (ΔE) and the additive concentration as illustrated in FIGS. 4 to 6, the concentration of the additives e.g., the extreme pressure agent, in the lubricant can be determined. Accordingly, according to a result of measurement of chromaticity stored chronologically, the consumption speed of the additives can be calculated. Here, when the additive concentration becomes about half of that of a new one, the performance of the lubricant falls below a permissible range. Such threshold value can be determined experimentally.

In the present example, in processing S610, the threshold value is set to 50, and a point of time when the concentration estimated from the chronologically stored additive concentration measurement results becomes 50 is estimated to be a replacement period. As the estimation method, publicly known various methods may be adopted. When an actual Measurement value such as those illustrated in FIG. 3 is obtained, on the basis of the assumption that the concentration decreases monotonically, a publicly known data extrapolation method can be used. In addition, when the concentration further transitions complicatedly, a publicly known method such as function fitting (curve fitting) can be used.

Note that, in the present example, the chronological chromaticity data measured by the optical sensor is stored and, on the basis of this, the degree of deterioration of the lubricant is estimated. In other words, it can be said that the degree of deterioration of the lubricant is estimated on the basis of a relative comparison between aging changes of R, G, and B in the chromaticity data.

Figure 13:
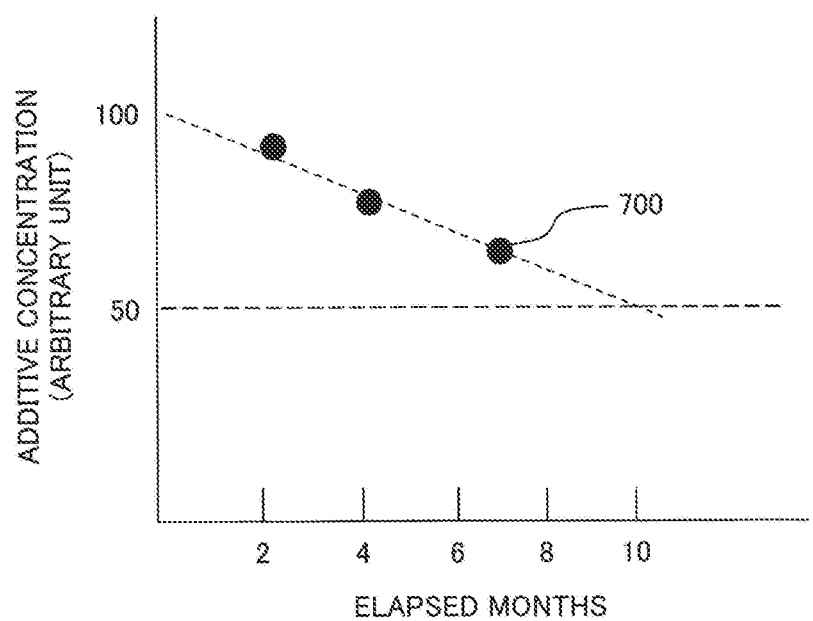
FIG. 13 is a graph illustrating a concept of lubricant remaining life estimation.
Figure 14:
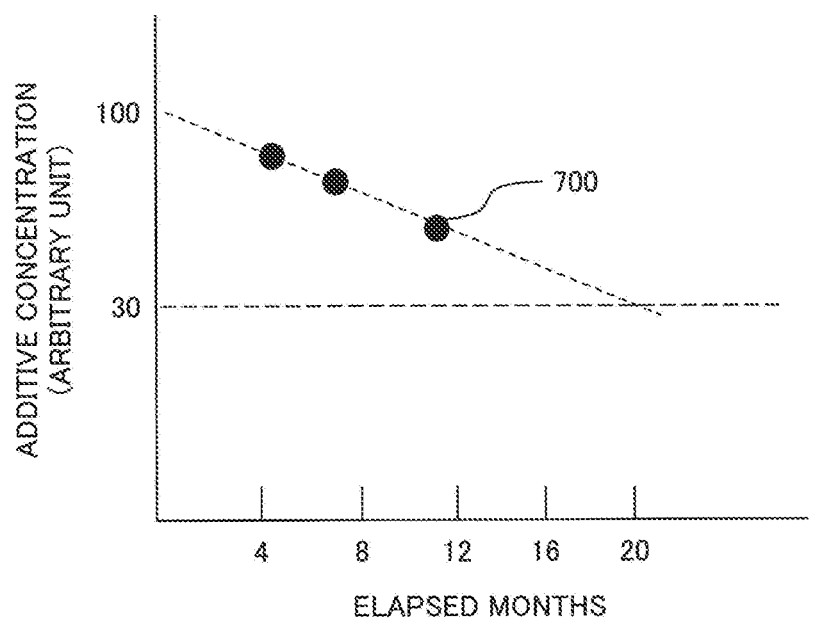
FIG. 14 a graph illustrating a concept of lubricant remaining life estimation.

A replacement period estimation result by processing S610 can be indicated as a lubricant diagnosis result (processing S611). In FIGS. 13 and 14, the vertical axis indicates additive concentration determined from the chromaticity, indicating a relationship between the additive concentration and the elapsed time. FIGS. 12 to 14 illustrate an example of indication of a result by processing S610.

In the example of FIG. 12, the additive indicates TPPT. It is estimated that the chromaticity reaches 300 after about 50 months. When the chromaticity is 300, the TPPT concentration is 50. Therefore, it is sufficient if a previous point (e.g., half a month ago) is set to a new replacement period. In processing S613, processing of one cycle ends. In processing S602 of a next cycle, determination processing is performed according to the new replacement period.

In the example of FIG. 13, the additive is ZnDTP, and the concentration becomes 50 after about 10 months from replacement to a new oil. Therefore, it is sufficient if a previous point (e.g., one month ago) is set to a new replacement period. In processing S613, processing of one cycle ends. In processing S602 of a next cycle, determination processing is performed according to the new replacement period.

In the example of FIG. 14, the additive is BHT, and the threshold value of BHT is 30. The concentration becomes 30 after about 20 months from replacement to a new oil. Therefore, it is sufficient if a previous point (e.g., one month ago) is set to a new replacement period. In processing S613, processing of one cycle ends. In processing S602 of a next cycle, determination processing is performed according to the new replacement period.

Note that, for example, after S611, the chromaticity data measured by the optical sensor can be converted into colors and display the colors on a display screen for the lubricant diagnosis results. When the state of the deterioration of the lubricant is displayed by colors on the display screen, the worker can visually recognize the state of deterioration of the lubricant. This helps the worker, for example, to visually check with eyes the state of the lubricant at the site to roughly understand the state of deterioration of the lubricant.

As described above, according to the present example, when the consumption speed of the additives in the lubricant is known using the additive concentration measurement results, the life of the lubricant can be detected early. Therefore, maintenance such as appropriate lubricant replacement enables prevention of an abnormality of the wind power generator. In addition, the lubricant replacement period can also be optimized. In addition, the additive concentration can be measured by a brief method, and when the optical sensor is installed in the nacelle, the deterioration of the additives in the lubricant can be remotely monitored online.

Note that, in the present example, on the basis of the chromaticity measured by the optical sensor, sign diagnosis of contamination due to abrasion powder or sign diagnosis of water entry can also be performed online.

Figure 15:
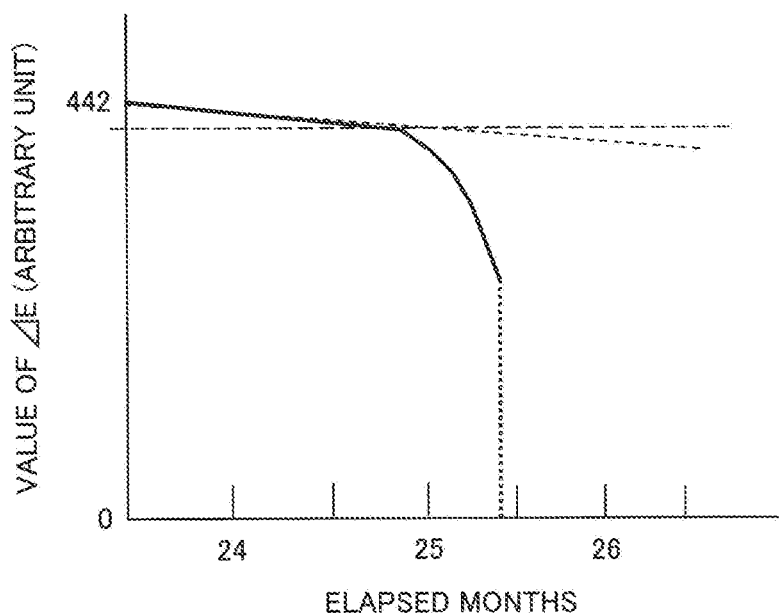
FIG. 15 a graph illustrating an example of detection of abrasion powder in a lubricant by an optical sensor.
Figure 16:
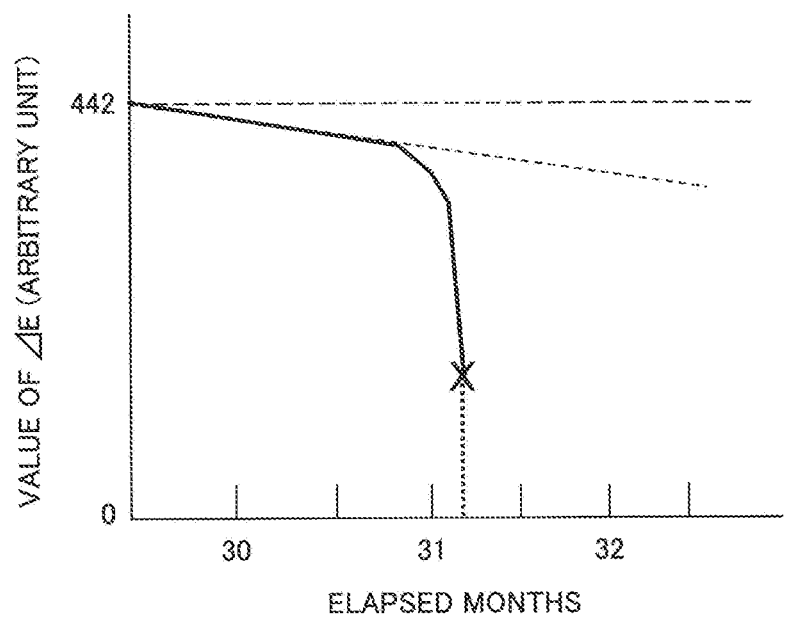
FIG. 16 is a graph illustrating an example of detection of entry of water into a lubricant by an optical sensor.

FIG. 15 illustrates an example of detection of abrasion powder in the lubricant by the optical sensor, and FIG. 16 illustrates an example of detection of water entry in the lubricant by the optical sensor. The vertical axes indicate chromaticity (ΔE) and the horizontal axes indicate elapsed months. As can be seen from these drawings and FIG. 8, unlike a monotonous reduction in ΔE for deterioration of the additives, abrasion powder or water entry exhibits an abrupt change in LE. That is, when ΔE deviates from a monotonous reduction, abrasion powder or water entry abruptly increases thereafter. Accordingly, when LE deviates from a monotonous reduction, it is considered to perform early replacement of the lubricant. In this way, in the present example, the deterioration of the additives and the contamination of the lubricant are both measured to be able to perform sign diagnosis for the lubricant. In addition, when ΔE deviates from a monotonous reduction, it is also effective to perform sign diagnosis regarding an abrupt increase in abrasion powder or water entry also for output of another sensor.

In the present example, the monitoring method and system that installs the optical sensor in the lubricant for the rotating component are described. However, the lubricant in the rotating component may be collected at the time of inspection, and may be measured by the optical sensor outside the rotating component such that the same diagnosis is performed.

EXAMPLE 2

In Example 2, an example is indicated in which data obtained from the sensor is used to correct estimation of the life of lubricant. In Example 1, it is assumed that the operation situation of the wind power generator 1 is constantly unchanged. However, in practice, the operation situation of the wind power generator 1 is not constant, but the situation varies with various factors.

For example, artificial variations in operation situations include a stop period of an apparatus for inspection and an operation adjustment for adjusting the amount of power generation. These variation parameters can be acquired as operation parameters of the wind power generator 1.

In addition, nature-origin factors of variations in operation situations include those internal and external to a wind power generation apparatus such as weather, temperature, humidity, such as wind speed. These factors of variations in operation situations can be measured by various sensors. Accordingly, when they are reflected as sensor data, it is possible to determine and predict the state of the lubricant more accurately.

As described in FIGS. 9 and 10, the various sensors can be installed in the wind power generator. Sensor data from the sensor group 304 is transmitted to the aggregation server 220 or the central server 240 via the server 210. In addition, the operation parameters of the wind power generator 1 can be obtained from the server 210, the aggregation server 220, or the central server 240 that performs such control.

Referring back to FIG. 11, description is given of the lubricant monitoring method that reflects operation situations. Basic processing is similar to that of FIG. 11. However, in diagnosis processing using sensor data (S604), sensor data or operation parameters are chronologically stored and are used for replacement period estimation and updating processing (S610).

For the sake of simplification of description, this example is directed to a mechanism of supplying a lubricant to a bearing portion, and as operation parameters indicative of operation situations, control parameters of the shaft rotation rate R (rpm) are used. Sensor data and operation parameters are not limited thereto, but other various matters can be used. In the present example, data of various sensors is aggregated to the central server 240 and is collectively processed there, but it is not limited thereto.

The central server 240, in replacement period estimation and updating processing (S610), acquires additive concentration measurement results input in processing S609 and control parameters of the shaft rotation rate R stored in processing S604. These data is chronologically stored together with time data in the storage apparatus.

Now, as a simple example, it is assumed that a reduction in, i.e., consumption of, concentration of the extreme pressure agent relates to the shaft rotation rate R (rpm). On the basis of this assumption, concentration $C(t)$ of the extreme pressure agent can be understood to be a function of time t and shaft rotation rate R. Therefore, the equation is as follows: $f(t,R)=C(t)$. By an experiment or situation, or on the basis of data of previous t, R, and the concentration of extreme pressure agents, function $f(t,R)$ can be modelled. Thus, in replacement period estimation and updating processing (S610), for future prediction of $C(t)$, a change in shaft rotation rate R is reflected. A result is displayed, for example, on a display apparatus.

Figure 17:
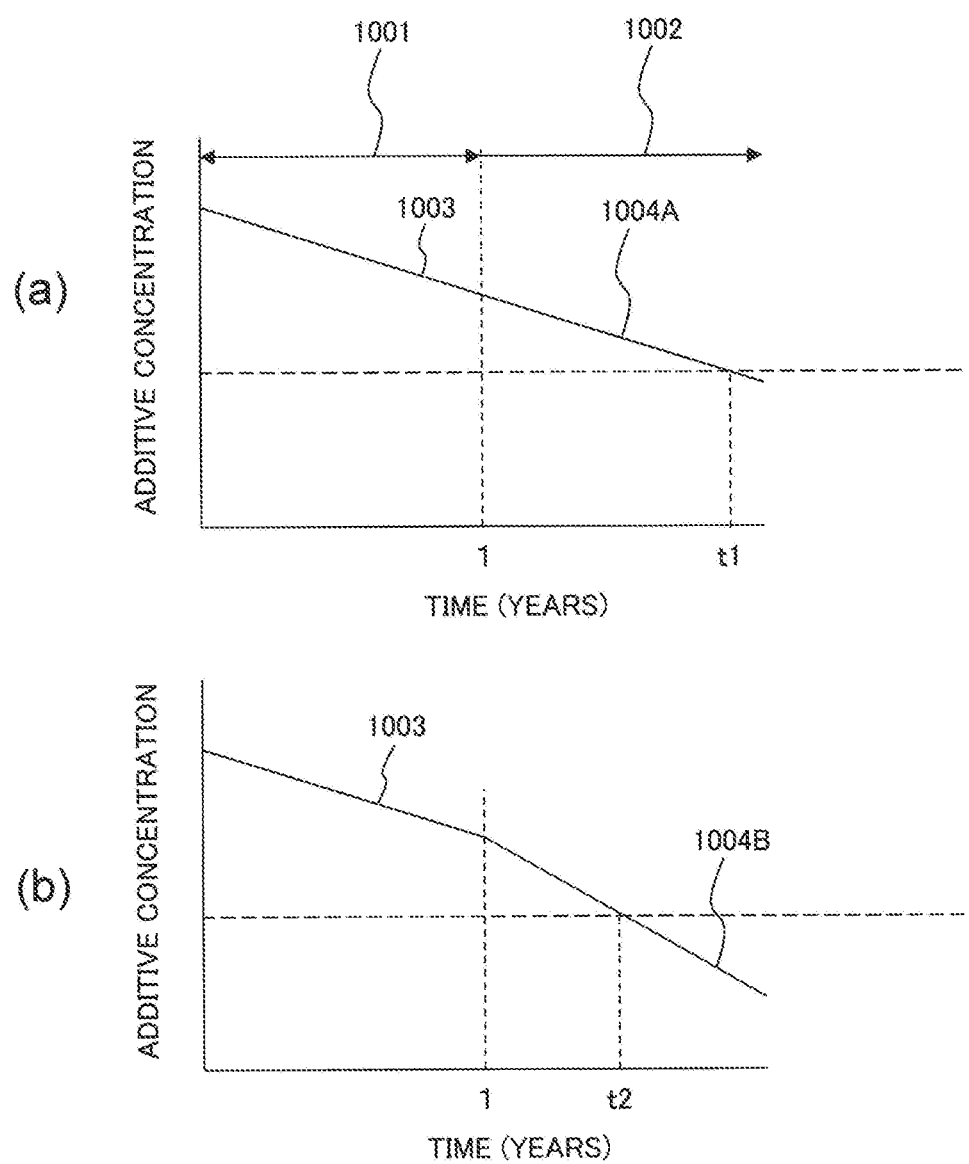
FIG. 17 is a graph illustrating a concept of lubricant remaining life estimation according to another example.

FIG. 17 is a graph illustrating an example of predicting and displaying a future value 1002 on the basis of data 1001 for the previous one year of the wind power generator 1. One year previous data 1003 is an actual measurement value. Feature data 1004A and 1004B is a prediction value.

In FIG. 17(a), future operation situations are unchanged and the rotation rate R is always constant. In this case, future value (prediction data) 1002 of the extreme pressure agent concentration transitions in the same way as the data 1001 for the previous one year. In this case, a limit of the extreme pressure agent concentration is predicted to reach at the point of time of t1.

In FIG. 17(b), future operation situations are changed, and the rotation rate R after elapse of one year is twice as that of the previous one year. Here, when it is assumed that the consumption speed of the extreme pressure agent is proportional to the rotation rate R, the prediction data of the extreme pressure agent concentration does not transition in the same way as the previous one year. For example, as indicated at 1004B of FIG. 17(b), a reduction rate increases. In this case a limit of the extreme pressure agent concentration is predicted to reach at the point of time of t2 that is shorter than t1.

In the above, the shaft rotation rate R used as an operation parameter to correct the estimated consumption speed of the additives, but sensor data may be used. For example, a reduction in concentration of the extreme pressure agent is considered to relate to temperature T(° C.) of the lubricant. On the basis of this assumption, the concentration $C(t)$ of the extreme pressure agent is understood to be a function of time t and temperature T. Similar to the case of the shaft rotation rate R, the estimated consumption speed of the extreme pressure agent can be corrected.

As in the example illustrated in FIG. 17, when operation parameters or sensor data that indicate operation situations of the wind power generator are reflected on the prediction data, it is possible to more accurately determine the timing at which parameters indicative of the lubricant quality such as extreme pressure agent concentration exceeds a threshold value. That is, future extreme pressure agent concentration can be determined more accurately on the basis of previous extreme pressure agent concentration, previous operation parameters (or sensor data), and future operation parameters (or prediction sensor data).

Among the parameters indicating operation situations, with regard to artificially controllable parameters such as operation time and power generation target value, future data can be prepared according to an operation schedule or the like. Therefore, when parameters indicating operation situations are used for prediction of an additive concentration indicating the lubricant quality, the prediction precision can be increased.

In addition, With regard to artificially uncontrollable parameters such as weather and temperature, future data can be predicted from previous result data. Therefore, similarly, when parameters indicating operation situations are used for prediction of an additive substance concentration indicating the lubricant quality, the prediction precision can be increased.

Figure 18:
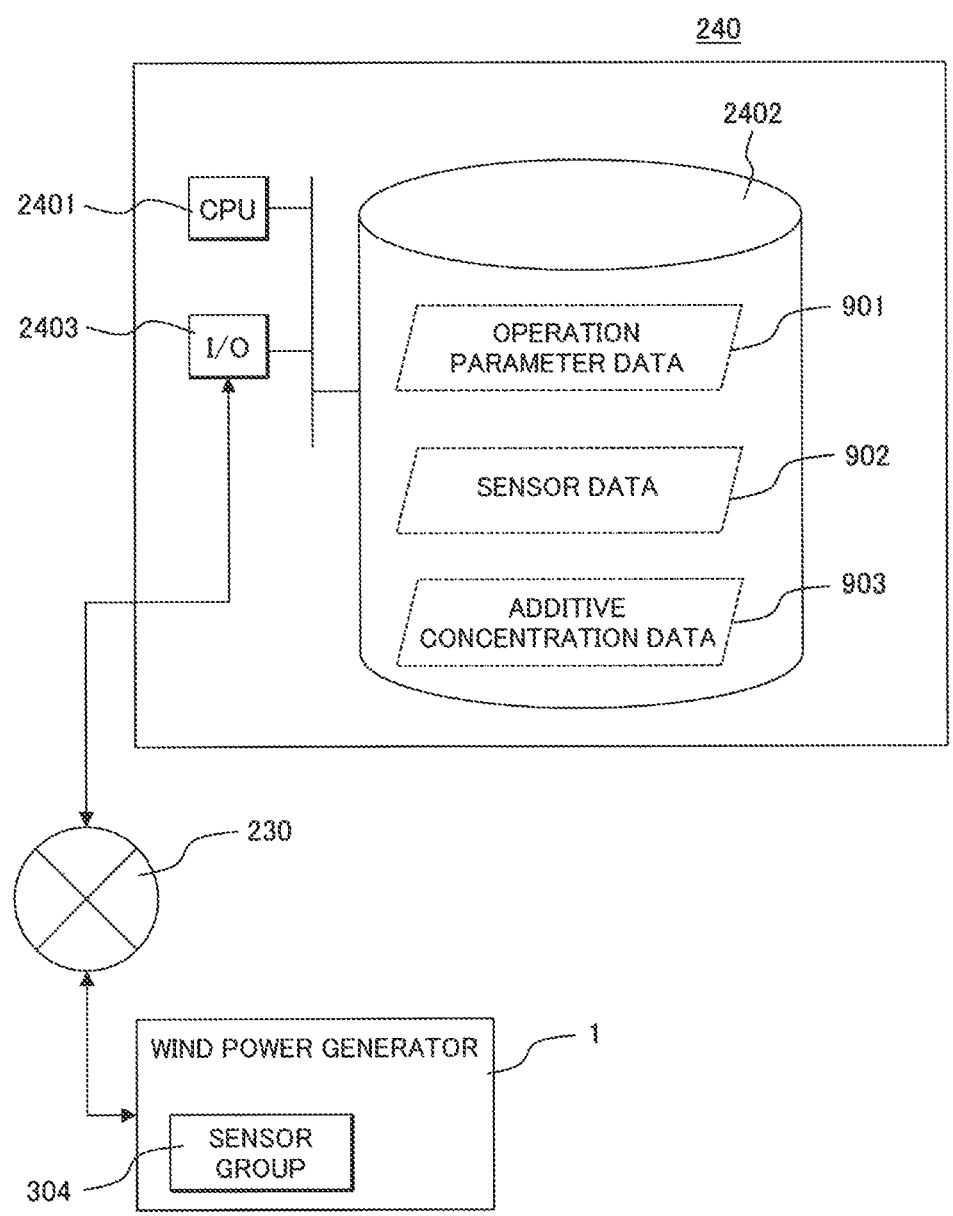
FIG. 18 is a block diagram illustrating an example of a central server of another example.

FIG. 18 is a block diagram illustrating a configurational example of the central server 240 of the present example. The central server 240 includes a basic server configuration including a processing apparatus 2401, a storage apparatus 2402 (e.g., a magnetic disk apparatus and a semiconductor memory), and an input/output apparatus 2403. The input/output apparatus 2403 includes an input apparatus such as a general keyboard or mouse, and an output apparatus such as an image display apparatus or a printer. In addition, the input/output apparatus 2403 includes a network interface that exchanges data, via the network 230, with the wind power generator 1, and its server 210 and aggregation server 220, or an additive quantifying analysis system (illustration omitted), e.g., a liquid chromatography mass spectrometer.

From the wind power generator 1 and its sensor group 304, various operation parameters or sensor data is input to the central server 240 directly or via the server 210 or the aggregation server 220. Alternatively, it may be input to the central server 240 not via the network, but via a portable recording medium. Such data is stored as chronological operation parameter data 901 or as chronological sensor data 902 in the storage apparatus 2402. In addition, in the present example, as one of the sensor group 304, for example, an optical sensor that includes a visible light source and a reception element and measures the chromaticity of the lubricant is used.

According to the lubricant chromaticity obtained by the optical sensor, a correlation between the chromaticity (RE) and the additive concentration such as those illustrated in FIGS. 4 to 6 is used to quantify the additive concentration in the lubricant.

Additives to be quantified are specifically one or more additives selected from an oil agent such as a higher fatty acid, higher alcohol and amine, ester, metal soap; an anti-wear agent such as zinc dialkyldithiophosphate (ZnDTP, also called ZDDP); an extreme pressure agent such as lead naphthenate, sulfurized palm oil, sulfurized fatty ester, dibenzyldisulfide, alkylpolysulfide, olefin polysulfide, xanthic sulfide, chlorinated paraffin, methyl trichlorostearate, lead naphthenate, amine alkylthiophosphate, chloroalkyl xanthate, triphenyl phosphorothionate (TPPT); a phenol derivative (e.g., 2,6-di-tert-butyl p-cresol (BHT), 2,6 di-tert-butyl p-phenol (DBP), 4,4'-methylene bis(2,6-dialkylphenol)), an amine derivative (e.g., 2,6-dialkyl-α-dimethylaminoparacresol, 4,4'-tetramethyldiaminodiphenylmethane, octylated phenylnaphthylamine, di-octyl-diphenylamine, dinonyl-diphenylamine, phenothiazine 2,2,4-trimethyldihydroxyquinizarin), an antioxidant such as metal dithiophosphate, alkyl sulfide, or the like, 1,4-dioxydianthraquinone (also known as: quinizarin), 1,2-dioxydianthraquinone (also known as: alizarin), benzotriazole, alkylbenzotriazole.

For example, when additives such as ZnDTP (ZDDP) and BHT having different functions are quantified using a correlation between the chromaticity (ΔE) and the additive concentration such as that illustrated in FIG. 6, and the result is used for diagnosis, more accurate diagnosis can be performed.

The processing apparatus 2401 uses the additive concentration data 903 and, as necessary, the operation parameter data 901 and the sensor data 902, which are stored in the storage apparatus 2402, to predict the consumption speed of the additive concentration and outputs it to the output apparatus. According to the present example, by reflecting operation parameters or sensor data indicating operation situations, it is possible to more accurately determine the timing when the parameters indicating the lubricant quality such as extreme pressure agent concentration exceeds the threshold value.

Figure 19:
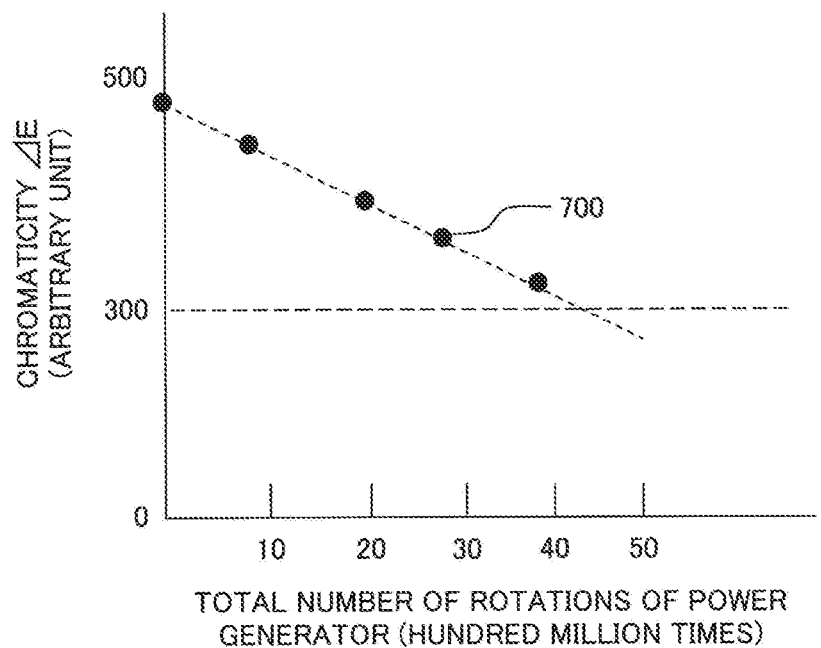
FIG. 19 is a graph illustrating a concept of lubricant remaining life estimation according to another example.
Figure 20:
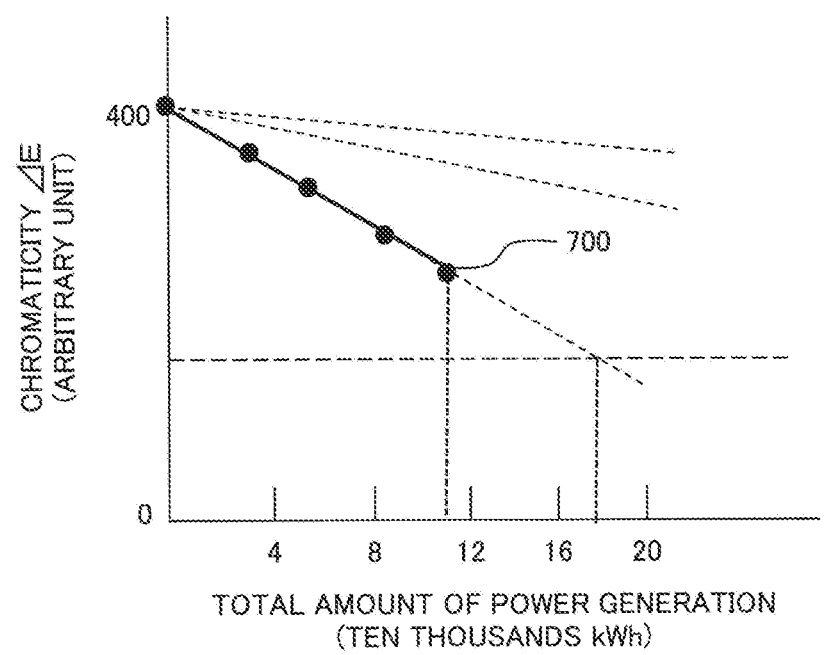
FIG. 20 is a graph illustrating a concept of lubricant remaining life estimation according to another example.

In the example illustrated in FIG. 17, the estimated consumption speed, e.g., of the extreme pressure agent, is corrected according to the operation parameters indicating operation situations. However, the horizontal axis may indicate, instead of elapsed period, the total number of rotations of the power generator (FIG. 19) or the total amount of power generation (FIG. 20), which is wind turbine operation information. Also, according to the present example, it is possible to more accurately determine the timing when parameters indicating the lubricant quality such as extreme pressure agent concentration exceeds a threshold value.

As described above, in the present example, in order to appropriately monitor the lubricant used for the main shaft, the generator, important rotating components (bearings) such as yaw and pitch, and the speed increaser of the wind power generator, the concentration of the additives is measured. In addition, the sensor is installed near the oil discharge port of the rotating component including an automatic lubricant supply mechanism to enable steady monitoring (online monitoring). In addition, parameters of operation situations of the wind power generator are monitored to enable more accurate prediction diagnosis. Thus, it is possible to predict the lubricant replacement period in an early stage, and, as a result, the stop time of the wind power generator is shortened, thereby reducing the maintenance cost and increasing the amount of power generation.

Note that the present invention is not limited to the aforementioned examples, but may include various variations.

For example, the aforementioned examples are described in detail to describe the present invention to be easily understood, and are not necessarily limited to include all the configurations described. In addition, part of the configuration of an example can be replaced with the configuration of another example. In addition, the configuration of another example can be added to the configuration of an example. In addition, regarding Part of the configuration of each example, addition, deletion, and replacement of another configuration can be performed.

For example, in the aforementioned examples, the description was given using the wind power generator as an example of the rotating machine. However, the present invention can also be applied to diagnosis of the deterioration of additives of a lubricant for a rotating machine such as a nuclear power generator, a thermal power generator, a geared motor, a railcar wheel flange, a compressor, a transformer, a movable plant machine, and a large pump machine.

REFERENCE SIGNS LIST

1 . . . wind power generator, 2 . . . tower, 3 . . . nacelle 3, 4 . . . hub, 5 . . . blade, 33 . . . speed increaser, 34 . . . generator, 37 . . . oil tank, 210 . . . server, 220 . . . aggregation server, 230 . . . network, 240 . . . central server, 301 . . . lubricant supply device, 302 . . . rotating component, 303 . . . measurement portion, 304 . . . sensor group, operation parameter data 901, sensor data 902, additive concentration data 903.

The invention claimed is:

1. A method for diagnosing deterioration of a lubricant including an extreme pressure agent as an additive, the method comprising:
   obtaining a preliminarily determined correlation between a concentration of the extreme pressure agent contained in the lubricant having different degrees of deterioration of the extreme pressure agent and chromaticity data determined based on measurement data of first optical sensor regarding the lubricant having different degrees of deterioration of the extreme pressure agent;
   in diagnosis of deterioration of the lubricant, obtaining chromaticity data of the lubricant subject to deterioration diagnosis by a second optical sensor, and quantifying the concentration of the extreme pressure agent contained in the lubricant subject to deterioration diagnosis based on the chromaticity data of the lubricant subject to deterioration diagnosis and the preliminarily determined correlation, and
   further diagnosing deterioration of the lubricant by distinguishing between consumption of the extreme pressure agent and lubricant contamination based on the chromaticity data of the lubricant subject to deterioration diagnosis.

2. The method for diagnosing deterioration of a lubricant according to claim 1, wherein the lubricant containing the extreme pressure agent as an additive is used for lubrication of a rotating component of a wind power generator, and the second optical sensor is installed in a nacelle of the wind power generator, the lubricant in the rotating component is measured by the second optical sensor, measurement data is transmitted to a server external to the wind power generator, the server storing the preliminarily determined correlation, and a concentration of an additive contained in a lubricant subject to deterioration diagnosis is quantified in the external server.

3. The method for diagnosing deterioration of a lubricant according to claim 1, wherein when all values of R, G, and B in chromaticity data of the lubricant subject to deterioration diagnosis are lower than RGB values of a new lubricant, it is determined that the lubricant subject to deterioration diagnosis is contaminated.

4. A system for monitoring a lubricant including an extreme pressure agent as an additive supplied to a drive portion of a rotating machine, the system comprising:
   an optical sensor that measures data regarding chromaticity of the lubricant, an input apparatus, a processing apparatus, a storage apparatus, and an output apparatus, wherein
   the processing apparatus quantifies a concentration of the extreme pressure agent contained in the lubricant subject to monitoring based on a preliminarily determined relationship between the concentration of the extreme pressure agent contained in the lubricant having different degrees of deterioration for the extreme pressure agent and chromaticity data by the optical sensor for the lubricant having different degrees of deterioration of the extreme pressure agent, and chromaticity data of the lubricant subject to monitoring obtained by the optical sensor,
   the storage apparatus chronologically stores concentration data of the extreme pressure agent contained in the lubricant subject to monitoring quantified by the processing apparatus,
   the processing apparatus estimates a time when a concentration of the extreme pressure agent contained in the lubricant subject to monitoring becomes a predetermined threshold value based on extreme pressure agent concentration data chronologically stored in the storage apparatus,
   the output apparatus outputs the time of becoming the predetermined threshold value obtained through estimation by the processing apparatus, and
   the processing apparatus further diagnoses deterioration of the lubricant by distinguishing between consumption of the extreme pressure agent and lubricant contamination based on the chromaticity data of the lubricant subject to monitoring obtained by the optical sensor.

5. The system for monitoring a lubricant of a rotating machine according to claim 4, wherein
   the rotating machine is a wind power generator, and
   the optical sensor is installed in a nacelle to measure a lubricant of a rotating component in the nacelle of the wind power generator.

6. The system for monitoring a lubricant of a rotating machine according to claim 4, wherein
   when all values of R, G, and B in chromaticity data of the optical sensor for the lubricant subject to monitoring are lower than RGB values of a new lubricant, it is determined that the lubricant subject to monitoring is contaminated.

7. The system for monitoring a lubricant of a rotating machine according to claim 4 wherein the storage apparatus chronologically stores operation parameters of the rotating machine, and
   the processing apparatus, based on operation parameters chronologically stored in the storage apparatus, corrects and estimates a time when a concentration of an additive contained in the lubricant subject to monitoring becomes a predetermined threshold value.

8. The system for monitoring a lubricant of a rotating machine according to claim 7, wherein the rotating machine is a wind power generator, and the operation parameter is at least one selected from a total operation time, a total amount of power generation, and a total number of rotations of the rotating machine.

9. The system for monitoring a lubricant of a rotating machine according to claim 4, wherein the output apparatus includes a display apparatus and displays a color of a lubricant subject to monitoring on the display apparatus by converting chromaticity data of a lubricant subject to monitoring obtained by the optical sensor.

10. A method for monitoring a lubricant of a rotating machine, the method comprising:
obtaining a preliminarily determined correlation between a concentration of an additive contained in the lubricant having different degrees of deterioration of the additive and chromaticity data determined based on measurement data of a first optical sensor regarding the lubricant having different degrees of deterioration; and
in diagnosis of deterioration of the lubricant, obtaining chromaticity data of the lubricant subject to deterioration diagnosis by a second optical sensor, and quantifying a concentration of the additive contained in the lubricant subject to deterioration diagnosis based on the chromaticity data of the lubricant subject to deterioration diagnosis and the preliminarily determined correlation, and
measuring in a first step a concentration of an additive contained in a lubricant subject to monitoring by the optical sensor;
chronologically storing in a second step a concentration of the additive measured in the first step in a storage apparatus to obtain chronological additive concentration data; and
estimating in a third step a time when a concentration of the additive becomes a predetermined threshold value based on chronological additive concentration data stored in the second step.

11. The method for monitoring a lubricant of a rotating machine according to claim 10, comprising:
a fourth step that chronologically stores an operation parameter of the rotating machine in the storage apparatus to obtain chronological operation parameter data,
wherein in the third step, based on previous data of the additive concentration data, and previous data and future prediction data of the operation parameter data, future data of the additive concentration data is predicted.

12. The method for diagnosing deterioration of a lubricant according to claim 1, wherein
a concentration of the extreme pressure agent contained in the lubricant is estimated based on a value of B in the chromaticity data.

13. The method for diagnosing deterioration of a lubricant according to claim 1, wherein
a degree of contamination of the lubricant and a concentration of the extreme pressure agent contained in the lubricant are estimated based on R, G, and B in the chromaticity data.

14. The A method for diagnosing deterioration of a lubricant the method comprising:
obtaining a preliminarily determined correlation between a concentration of an additive contained in the lubricant having different degrees of deterioration of the additive and chromaticity data determined based on measurement data of a first optical sensor regarding the lubricant having different degrees of deterioration; and
in diagnosis of deterioration of the lubricant, obtaining chromaticity data of the lubricant subject to deterioration diagnosis by a second optical sensor, and quantifying a concentration of the additive contained in the lubricant subject to deterioration diagnosis based on the chromaticity data of the lubricant subject to deterioration diagnosis and the preliminarily determined correlation, and
wherein concentrations of a plurality of types of additives that are contained in the lubricant and have different chromaticity change properties are estimated based on the chromaticity data.

15. A system of a rotating machine including the system for monitoring a lubricant of a rotating machine according to claim 4.

* * * * *